United States Patent [19]

Fayerman et al.

[11] Patent Number: 4,513,086
[45] Date of Patent: Apr. 23, 1985

[54] CLONING VECTORS FOR USE IN STREPTOMYCES AND RELATED ORGANISMS

[75] Inventors: Jeffrey T. Fayerman; Mark A. Richardson, both of Indianapolis, Ind.

[73] Assignee: Eli Lilly and Company, Indianapolis, Ind.

[21] Appl. No.: 404,082

[22] Filed: Aug. 2, 1982

Related U.S. Application Data

[63] Continuation-in-part of Ser. No. 311,711, Oct. 15, 1981, abandoned.

[51] Int. Cl.³ .................. C12N 1/00; C12N 15/00; C12N 1/20; C12P 21/00; C12P 21/02; C12P 19/34; C07H 21/04
[52] U.S. Cl. .................. 435/317; 435/68; 435/70; 435/91; 435/172.3; 435/253; 536/27; 935/29; 935/75
[58] Field of Search .......... 435/68, 70, 91, 172, 435/253, 317, 886, 172.3; 536/27

[56] References Cited

U.S. PATENT DOCUMENTS

| | | | |
|---|---|---|---|
| 4,273,875 | 6/1981 | Manis | 435/253 |
| 4,332,898 | 6/1982 | Reusser | 435/253 |
| 4,332,900 | 6/1982 | Manis et al. | 435/253 |
| 4,338,400 | 7/1982 | Manis et al. | 435/253 |
| 4,340,674 | 7/1982 | Manis et al. | 435/253 |
| 4,342,829 | 8/1982 | Kastner et al. | 435/253 |

FOREIGN PATENT DOCUMENTS

WO79/01169 12/1979 PCT Int'l Appl.
2048894 12/1980 United Kingdom.

OTHER PUBLICATIONS

Hopwood et al.: in *Plasmids of Medical, Environmental and Commercial Importance*, Timmis et al., (ed.), Elsevier?North-Holland, 1979, pp. 245-258.
Bibb, M. et al., 1980, Nature 284:526.
Thompson, C. et al., 1980, Nature 286:525.
Thompson, C. and Cundliffe, E., 1980, J. of Bacteriology 142(2):455.
Bibb, M. et al., 1980, Developments in Industrial Microbiology, 21:55.
Gray O. et al., 1980, Abstracts of the 80th Annual ASM Meeting, Paper No. H68.
F. F. Nord, *Advances in Enzymology*, 1966, pp. 238-244.
H. Ogawara et al., *Antimicrobial Agents and Chemotherapy*, 13, 5, May, 1978, pp. 865-870.
H. Ogawara et al., *The Journal of Biological Chemistry*, 256, 6, Mar. 25, 1981, pp. 2649-2655.
H. Ogawara, *Antimicrobial Agents and Chemotherapy*, 8, 4, Oct. 1975, pp. 402-408.

Primary Examiner—Thomas G. Wiseman
Assistant Examiner—James Martinell
Attorney, Agent, or Firm—Gerald V. Dahling; Arthur R. Whale

[57] ABSTRACT

The present invention discloses selectable recombinant DNA cloning vectors for use in Streptomyces and related organisms.

97 Claims, 16 Drawing Figures

Restriction Site and Functional Map of Plasmid pEL103

Restriction Site and Functional Map
of Plasmid pEL103**

Restriction Site and Functional Map of Plasmid pLR1

Restriction Site and Functional Map
of Plasmid pLR2**

Restriction Site and Functional Map of Plasmid pLR4

Restriction Site and Functional Map of Plasmids pEL107 and pEL105 pEL 107 pEL 105

Restriction Site and Functional Map of Plasmids pEL108 and pEL104 pEL 108 pEL 104

Restriction Site and Functional Map of Plasmids pEL109 and pEL110 pEL 109 pEL 110

Restriction Site and Functional Map
of Plasmids pEL111 and pEL112** pEL 111 pEL 112

Restriction Site and Functional Map
of Plasmids pEL113 and pEL114**

Restriction Site and Functional Map of Plasmids pEL115 and pEL116 pEL 115 pEL 116

Restriction Site and Functional Map of Plasmids pEL117 and pEL118 pEL 117 pEL 118

Restriction Site and Functional Map
of Plasmids pEL119 and pEL120**

Restriction Site and Functional Map of Plasmids pEL121 and pEL122 pEL 121 pEL 122

Restriction Site Map of Plasmids pFJ124, pFJ144 and pFJ145

Restriction Site Map of Plasmids pFJ146 and pFJ147 pFJ146 pFJ147

Restriction Site Map of Plasmids
pFJ148, pFJ149, pFJ150, and pFJ151**

1. pFJ148
2. pFJ149

1. pFJ150
2. pFJ151

CLONING VECTORS FOR USE IN STREPTOMYCES AND RELATED ORGANISMS

CROSS-REFERENCE

This application is a continuation-in-part of our co-pending application, Ser. No. 311,711, now abandoned filed 10/15/81.

SUMMARY OF THE INVENTION

The present invention comprises novel recombinant DNA cloning vectors comprising a functional origin of replication-containing restriction fragment of plasmid pEL103 and one or more DNA segments that convey resistance to antibiotics. The invention further comprises transformants of the aforementioned vectors.

The present invention provides antibiotic resistance conferring cloning vectors for use in Streptomyces and related host cells. Heretofore, the development and exploitation of recombinant DNA technology in the above organisms has been retarded and made especially difficult because of the general lack of selectable genetic markers on cloning vectors. The vectors of the present invention are functional and selectable in both Streptomyces and other host strains and therefore represent a significant advance in the technical art.

The present vectors are particularly useful because they are small, versatile, and can be transformed and selected in any Streptomyces cell that is sensitive to an antibiotic for which resistance is conveyed. Since over half of the clinicially important antibiotics are produced by Streptomyces strains, it is desirable to develop cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the millions of cells, has acquired the plasmid DNA. This is important because DNA sequences that are non-selectable can be inserted onto the vectors and, upon transformation, cells containing the vector and the particular DNA sequence of interest can be isolated by appropriate antibiotic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a stable and heritable change in the recipient cell.

Transformant—a recipient host cell that has undergone transformation.

Sensitive Host Cell—a host cell that cannot grow in the presence of a given antibiotic without a DNA segment that confers resistance thereto.

Restriction Fragment—any linear portion or whole of a plasmid generated by the action of one or more restriction enzymes on the plasmid.

Insertional Isomer—one of the two or more possible recombinant DNA molecules formed when a DNA fragment is inserted at one of two or more compatible sites on the recipient DNA.

Plasmid pLR2 1.6 kb BamHI Restriction Fragment—the same 1.6 kb BamHI thiostrepton resistance-conferring fragment contained in plasmid pIJ6.

Plasmid pLR1 or pLR4 3.4 kb BamHI Restriction Fragment—the same 3.4 kb BamHI neomycin resistance-conferring fragment contained in plasmid pIJ2.

Amp ®—the ampicillin resistant phenotype.

$Tet^S$—the tetracycline sensitive phenotype.

Thio ®—the thiostrepton resistant phenotype.

Neo ®—the neomycin resistant phenotype.

DETAILED DESCRIPTION OF THE INVENTION

The present invention comprises recombinant DNA cloning vectors comprising:

(a) a functional origin of replication-containing restriction fragment of plasmid pEL103, and
(b) one or more DNA segments that convey resistance to at least one antibiotic when transformed into a sensitive host cell, said host cell being susceptible to transformation, cell division, and culture.

The invention further comprises transformants of the aforementioned vectors.

Figure 1:
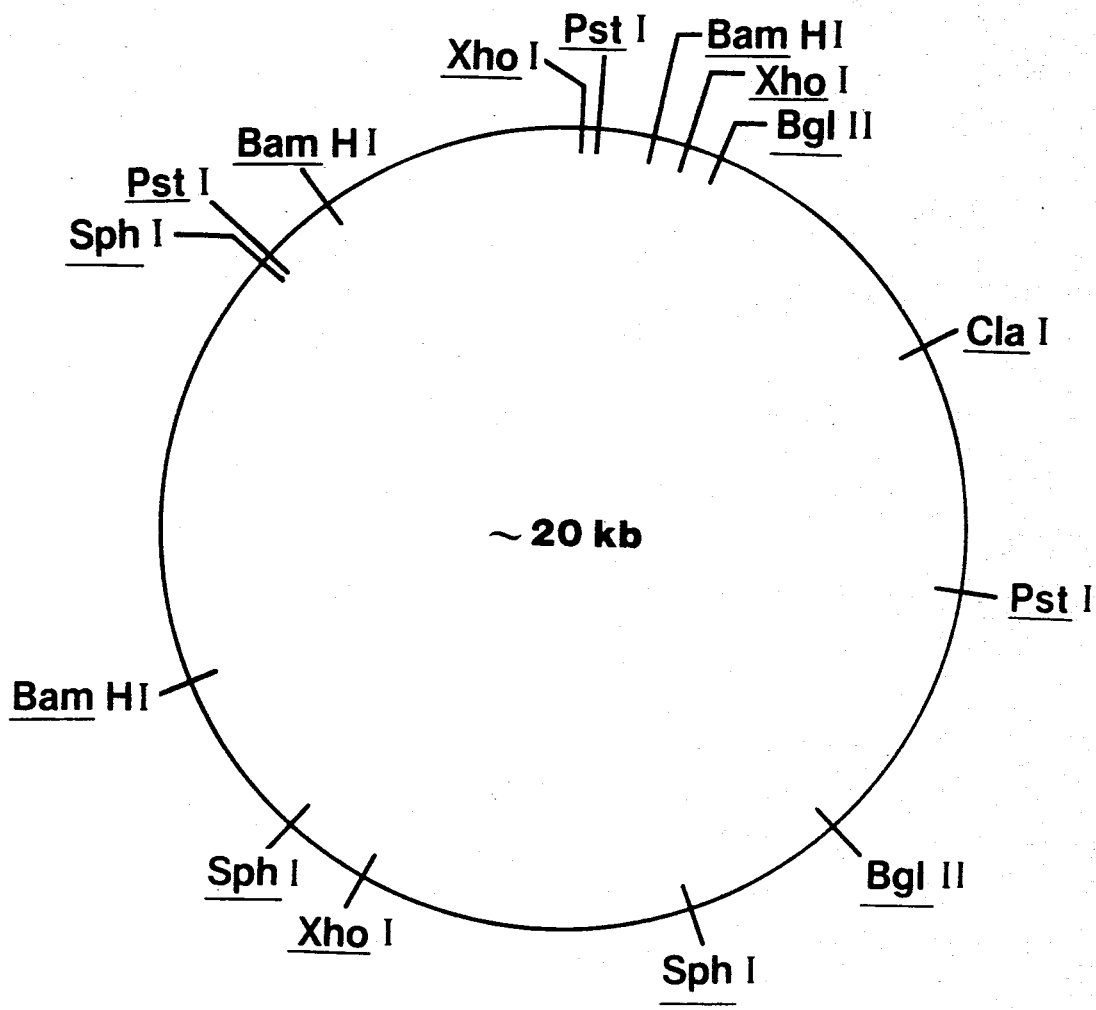

The vectors of the prsent invention are constructed by ligating one or more antibiotic resistance-conferring DNA segments onto an origin of replication-containing restriction fragment of plasmid pEL103. Plasmid pEL103, from which the origin of replication-containing fragments are constructed, is approximately 20.0 kb and contains several restriction sites which are particularly advantageous for molecular cloning. Since the origin of replication of plasmid pEL103 has been localized to within 2.8 kb BamHI restriction fragment, a variety of different origin of replication containing fragments can be generated by digesting the plasmid with restriction enzymes that cut outside the 2.8 kb BamHI region. A detailed restriction site and functional map of plasmid pEL103 is presented in FIG. 1 of the accompanying drawings. For purposes of the present application, FIG. 1 and all subsequent figures are not drawn to scale.

Plasmid pEL103 can be conventionally isolated from *Streptomyces granuloruber* No. A39912.13/pEL103, a strain deposited and made part of the permanent stock culture collection of the Northern Regional Research Laboratory, Peoria, Ill. It is available to the public, as a preferred source and stock reservoir of the plasmid, under the accession number NRRL 12549. *Streptomyces granuloruber* No. A39912.13/pEL103 is derived from *Streptomyces granuloruber* No. A39912, a strain also harboring plasmid pEL103 that has also been deposited at the above aforementioned stock culture collection under the accession number NRRL 12389.

Although many different origin of replication-containing fragments of plasmid pEL103 can be constructed, those exemplified herein for illustrative purposes include the 2.8 kb and 19.9 kb BamHI restriction fragments. These fragments are ligated to one or more antibiotic resistance-conferring DNA fragments, exemplified herein for illustrative purposes by the thiostrepton resistance-conferring 1.6 kb BamHI restriction fragment of plasmid pLR2 and the neomycin resistance-conferring 3.4 kb BamHI restriction fragment of plasmid pLR1 or plasmid pLR4, to form vectors illustrative of the present invention.

Figure 2:
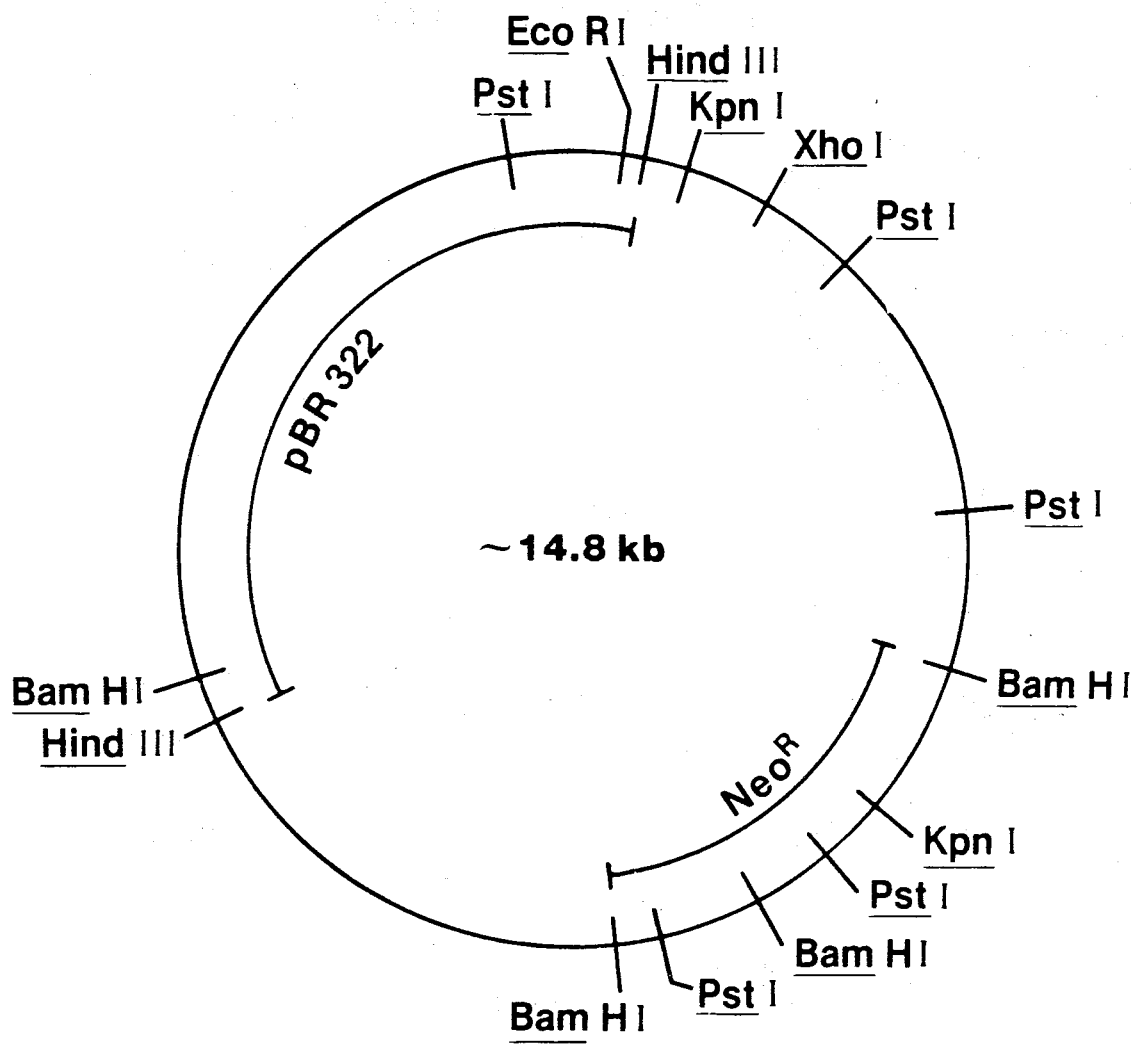
Figure 3:
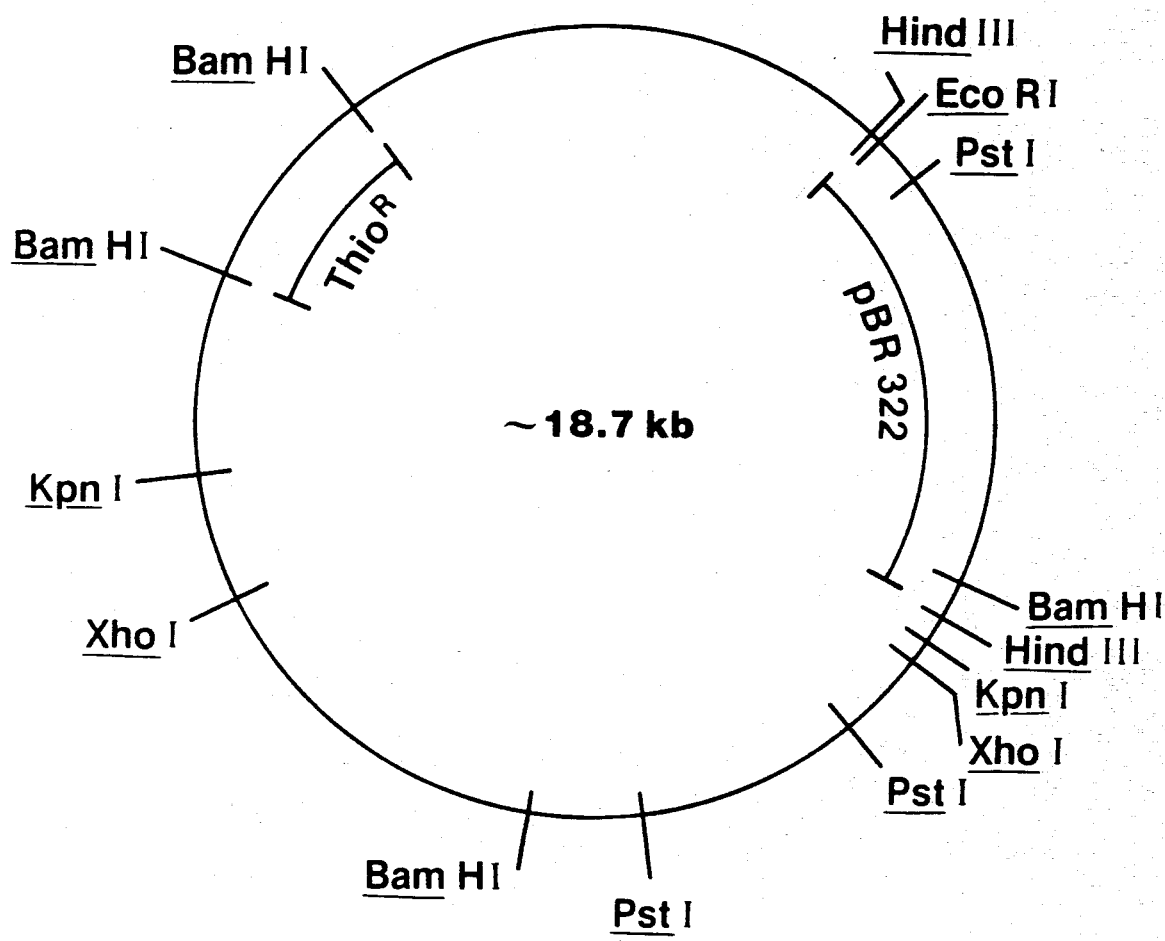
Figure 4:
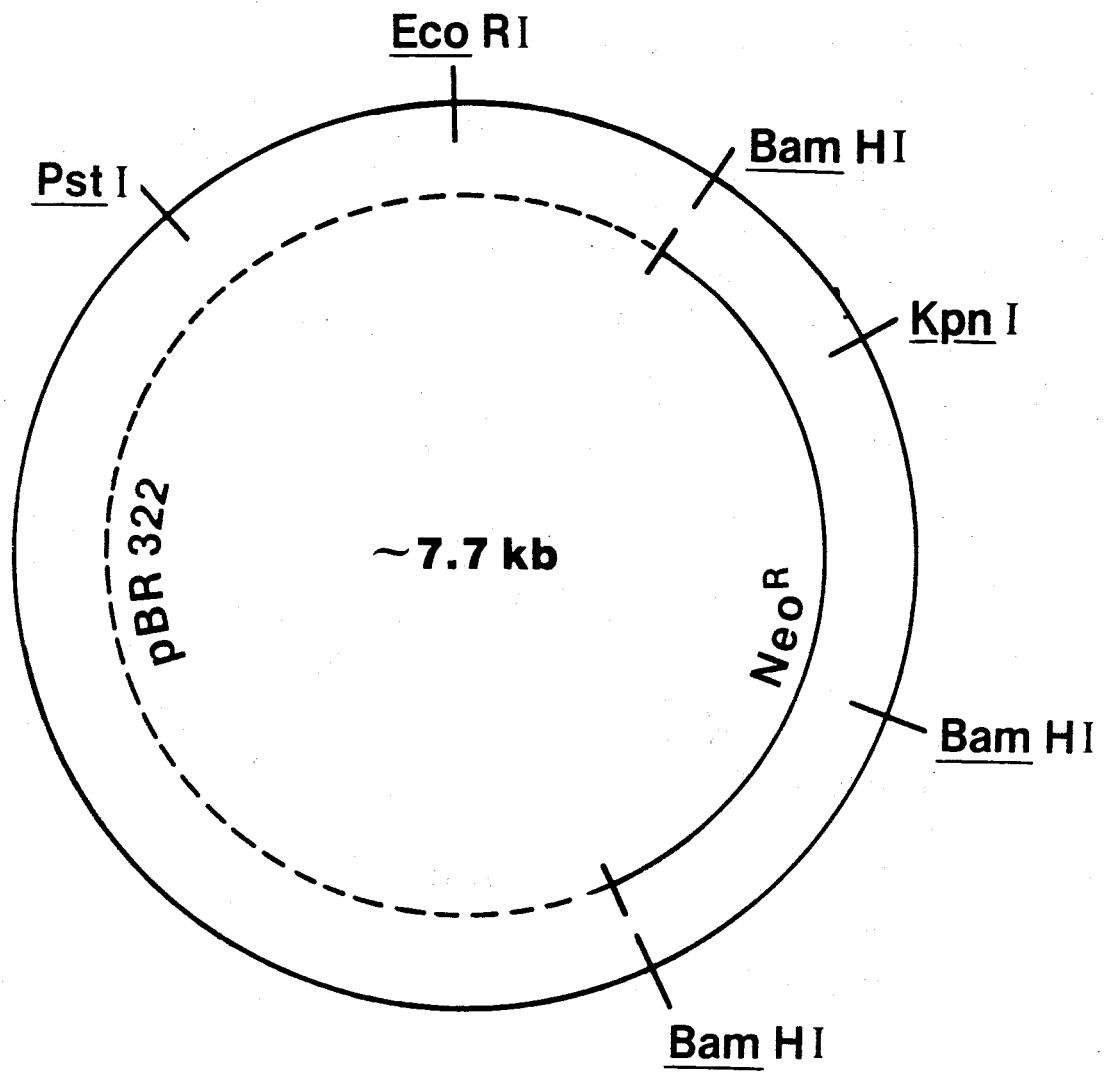

Plasmid pLR2, the source of the thiostrepton resistance-conferring fragment, is approximately 18.7 kb and is constructed by ligating HindIII treated plasmid pIJ6, disclosed in Thompson et al., 1980, Nature 286:525, to HindIII treated plasmid pBR322. Plasmid pLR1, the source of the neomycin resistance-conferring fragment, is approximately 14.8 kb and is similarly constructed, except that plasmid pIJ2, disclosed in Thompson et al., 1980, is used instead of plasmid pIJ6. Both plasmids pLR2 and pLR1 are functional in E. coli and therefore can be amplified and isolated conveniently for subsequent manipulation. An analogous construction, resulting in plasmid pLR4, is made by ligating BamHI treated plasmid pBR322 to BamHI treated plasmid pLR1. A restriction site and functional map of each of plasmids pLR1, pLR2, and pLR4 is presented respectively in FIGS. 2–4 of the accompanying drawings.

For convenience and ease of construction, the thiostrepton resistance-conferring 1.6 kb BamHI fragment and the neomycin resistance-conferring 3.4 kb BamHI fragment are ligated to the 2.8 kb or the 19.9 kb origin of replication-containing BamHI fragment of plasmid pEL103. The resulting recombinant DNA is then self ligated to produce plasmids illustrative of the present invention. Recombinant plasmids of two orientations results depending upon the orientation of the particular resistance conferring DNA fragment. Thus, ligation of the 1.6 kb BamHI fragment of plasmid pLR2 onto the 2.8 kb BamHI fragment of plasmid pEL103 results in illustrative plasmids pEL107 and pEL105; ligation of the 3.4 kb BamHI fragment of plasmid pLR1 or plasmid pLR4 results in illustrative plasmids pEL109 and pEL110; and ligation of both of the fragments results in illustrative plasmids pEL113, pEL114, pEL115, and pEL116. Similarly, ligation of the 1.6 kb BamHI fragment onto the 19.9 kb BamHI fragment of plasmid pEL103 results in illustrative plasmids pEL108 and pEL104; ligation of the 3.4 kb BamHI fragment results in illustrative plasmids pEL111 and pEL112; and ligation of both of the fragments results in illustrative plasmids pEL117, pEL118, pEL119, and pEL120.

Various plasmid pEL103 restriction fragments can be used for the ligation of antibiotic resistance-conferring DNA segments provided that the origin of replication contained in the 2.8 kb BamHI restriction fragment is present. Additional plasmid pEL103 restriction fragments, useful for constructing illustrative plasmids within the scope of the present invention, include, but are not limited to, the PstI, SphI, BglII, ClaI, and XhoI fragments. A particular antibiotic resistance-conferring DNA segment is not limited to a single position on a plasmid pEL103 fragment but can be ligated or inserted at varying sites provided that the origin of replication or other critical plasmid controlled physiological functions are not disrupted. Those skilled in the art understand or can readily determine which sites are advantageous for the ligation or insertion of a particular DNA segment.

Although the thiostrepton and neomycin antibiotic resistance-conferring DNA segments exemplified herein are respectively the 1.6 kb and 3.4 kb BamHI restriction fragments of plasmids pLR2 and pLR1, those skilled in the art can construct and use, either individually or in combination, additional DNA segments that also confer resistance to thiostrepton and neomycin. Additional thiostrepton resistance-conferring DNA segments of plasmid pLR2 include, for example, the 13 kb PstI restriction fragment and also the BclI subfragment of the 1.6 kb BamHI restriction fragment. Additional neomycin resistance-conferring DNA segments of plasmid pLR1 include, for example, the 3.5 kb PstI restriction fragment and also the larger of the SstI-KpnI subfragments of the 3.4 kb BamHI restriction fragment.

Still other DNA segments that confer resistance to the same or to different antibiotics such as, for example, chloramphenicol, streptomycin, hygromycin, viomycin, tylosin, erythromycin, and the like can also be constructed and used by those skilled in the art. Erythromycin resistance-conferring DNA segments include, for example, ~2.8 kb SalI, ~2.7 kb SalI-BglII, ~3.0 kb HindIII, ~2.5 kb SalI-BamHI, ~2.8 kb XhoI-BglII, and the ~4.1 kb EcoRI-BamHI restriction fragments of plasmid pIJ43. Plasmid pIJ43 can be obtained from E. coli 803/pIJ43, a strain deposited and made part of the permanent stock culture collection of the American Type Culture Collection, Rockville, Md. It is available to the public as a preferred source and stock reservoir of the plasmid under the accession number ATCC 39156.

Functional derivatives of the various antibiotic resistance-conferring DNA segments can be made by adding, eliminating, or substituting certain nucleotides in accordance with the genetic code. Those skilled in the art will understand that ligation of these modified segments, or any other antibiotic resistance-conferring DNA segment, to an origin of replication-containing fragment of plasmid pEL103 results in vectors that are also within the scope of the present invention.

Derivative vectors that further exemplify the invention can also be constructed. For example, BclI-BamHI deletion of plasmid pEL105 results in illustrative plasmid pFJ124, a plasmid from which additional derivatives can also be made. Thus, insertion of the plasmid pLR1 or pLR4 ~3.4 kb BamHI neomycin resistance-conferring fragment into plasmid pFJ124 results in illustrative plasmids pFJ144 and pFJ145; deletion (BclII-BamHI) of plasmid pFJ144 results in illustrative plasmid pFJ146; insertion of the plasmid pIJ43 ~2.7 kb SalI-BglII erythromycin resistance-conferring fragment into plasmid pFJ124 results in illustrative plasmid pFJ147; and similarly, insertion of the plasmid pIJ43 ~2.0 kb SalI erythromycin resistance-conferring fragment results in illustrative plasmids pFJ148 and pFJ149. The aforementioned antibiotic resistance-conferring derivative plasmids contain the pEL103 origin of replication and are therefore within the scope of the present invention.

The restriction fragments of plasmid pEL103 and the various antibiotic resistance-conferring DNA segments can be modified to facilitate ligation. For example, molecular linkers can be provided to a particular plasmid pEL103 restriction fragment or to an antibiotic resistance-conferring DNA segment. Thus, specific sites for subsequent ligation can be constructed conveniently. In addition, plasmid pEL103 and the pEL103 origin of replication-containing restriction fragments can also be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose.

The present vectors such as, for example, plasmid pEL103, pEL105, pEL109, pEL113, pEL111, pEL117, pFJ124, pFJ144, and pFJ147 can be ligated to a functional replicon-containing and antibiotic resistance-conferring restriction fragment of *E. coli* plasmids such as, for example, plasmids pBR322, pBR324, pBR325, pBR328 and the like, to produce novel bifunctional plasmids for use in *E. coli* and Streptomyces. These constructions, specifically exemplified herein by illustrative plasmids pEL121, pEL122, pFJ150 and pFJ151, are particularly advantageous because amplification and manipulation of plasmids can be done faster and more conveniently in *E. coli* than in Streptomyces. Thus, after desired recombinant DNA procedures are accomplished within the *E. coli* host system, the entire plasmid or the particular Streptomyces DNA can be removed, and re-constructed (if necessary) to plasmid form, and then transformed into a Streptomyces or related host cell.

The recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether, and glycopeptide antibiotics. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis*, *S. fimbriatus*, *S. halstedii*, *S. rochei* and *S. viridochromogenes* (cephalmycins A, B); *S. cattleya* (thienamycin); and *S. olivaceus*, *S. flavovirens*, *S. flavus*, *S. fulvoviridis*, *S. argenteolus*, and *S. sioyaensis* (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and can be transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present vectors are especially useful and can be transformed, include restrictionless cells of, for example: *S. coelicolor, S. granuloruber, S. roseosporus, S. lividans, S. tenebrarius, S. acrimycins, S. glaucenscens, S. parvilin, S. pristinaespiralis, S. violaceoruber, S. vinaceus, S. espinosus*, and *S. azureus*.

In addition to the representative Streptomyces host cells described above, the present vectors are also useful and can be transformed into cells of restrictionless strains of other taxa such as, for example: Bacillus, staphylococcus and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are more preferred than others. Accordingly, preferred vectors are plasmids pEL103, pEL105, pEL109, pEL113, pEL104, pEL111, pEL117, pEL121, pFJ124, pFJ144, pFJ146, pFJ147, pFJ151, pFJ153, pFJ155, and pFJ160; and preferred transformants are *Streptomyces ambofaciens*/pEL103, *S. ambofaciens*/pEL105, *S. ambofaciens*/pEL109, *S. ambofaciens*/pEL113, *S. ambofaciens*/pEL104, *S. ambofaciens*/pEL111, *S. ambofaciens*/pEL117, *E. coli* K12 HB101/pEL121, *S. ambofaciens*/pFJ124, *S. ambofaciens*/pFJ144, *S. ambofaciens*/pFJ146, *S. ambofaciens*/pFJ147, *E. coli* K12 HB101/pFJ150, *E. coli* K12 HB101/pFJ153, *E. coli* K12 HB101/pFJ155, and *E. coli* K12 HB101/pFJ160. Moreover, of this preferred group, plasmids pEL103, pEL105, pEL113, pEL109, pFJ124, pJF144, and pFJ147, and transformants *S. ambofaciens*/pEL103, *S. ambofaciens*/pEL105, *S. ambofaciens*/pEL113, *S. ambofaciens*/pEL109, *S. ambofaciens*/pFJ124, *S. ambofaciens*/pFJ144, and *S. ambofaciens*/pFJ147 are most preferred.

The recombinant DNA cloning vectors and transformants of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted onto the present vectors and then transformants containing the non-selectable DNA can be isolated by appropriate antibiotic selection. Such non-selectable DNA segments can be inserted at any site, except within regions necessary for plasmid function and replication, and include, but are not limited to, genes that specify antibiotic modification enzymes and regulatory genes of all types.

More particularly, a non-selectable DNA segment that comprises a gene is inserted on a plasmid such as for example, illustrative plasmid pEL113, at the central SalI restriction site of the 1.6 kb BamHI resistance-conferring fragment. Such an insertion inactivates the thiostrepton resistance gene and thus allows for the easy identification of transformants containing the recombinant plasmid. This is done by first selecting for neomycin resistance and, secondarily, identifying those neomycin resistant transformants that are not resistant to thiostrepton. In a similar manner, insertion of a DNA segment of interest at, for example, the internal BamHI restriction site of the 3.4 kb BamHI resistance-conferring fragment inactivates the neomycin resistance gene. Thus, transformants carrying this recombinant plasmid also are identified easily by first selecting for thiostrepton resistance and, secondarily, identifying those thiostrepton resistant transformants that are not resistant to neomycin. Therefore, the ability to select for antibiotic resistance in Streptomyces and related cells allows for the efficient isolation of the extremely rare cells that contain the particular non-selectable DNA of interest.

The functional test for antibiotic resistance, as described herein above, is also used to locate DNA segments that act as control elements and direct expression of an individual antibiotic resistance gene. Such segments, including but not limited to, promoters, attenuators, repressors, inducers, ribosomal binding sites, and the like, are used to control the expression of other genes in cells of Streptomyces and related organisms.

The thiostrepton and neomycin resistance-conferring vectors of the present invention are also useful for insuring that linked DNA segments are stably maintained in host cells over many generations. These genes or DNA fragments, covalently linked to the thiostrepton or neomycin resistance-conferring fragment and propagated either in Streptomyces or in the cells of related organisms, are maintained by exposing the transformants to levels of thiostrepton or neomycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Apramycin, Tobramycin, Erythromycin, and the like. The present invention also provides selectable vectors that are useful for cloning, characterizing, and reconstructing DNA sequences that code for commercially important proteins such as, for example, human insulin, human proinsulin, glucagon, interferon, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, Streptomycin, Cephalosporin, Tylosin, Actaplanin, Narasin, Monensin, Apramycin, Tobramycin, and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

*Streptomyces granuloruber* No. A39912.13/pEL103 can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces granuloruber* No. A39912.13/pEL103 is grown under aerobic culture conditions over a relatively wide pH range of about 5 to 9 at temperatures ranging from about 15° to 40° C. For production of plasmid pEL103 at highest copy number, however, it is desirable to start with a culture medium at a pH of about 7.2 and maintain a culture temperature of about 30° C. Culturing *Streptomyces granuloruber* No. A39912.13/pEL103 under the aforementioned conditions results in a reservoir of cells from which plasmid pEL103 can be isolated conveniently by techniques well known in the art.

The following examples further illustrate and detail the invention disclosed herein. Both an explanation of and the actual procedures for constructing the invention are described where appropriate.

EXAMPLE 1

Isolation of Plasmid pEL103

A. Culture of *Streptomyces granuloruber* No. A39912.13/pEL103

A vegetative inoculum of *Streptomyces granuloruber* No. A39912.13/pEL103 (NRRL 12549) was conventionally prepared by growing the strain under submerged aerobic conditions in 50 ml. of sterilized trypticase soy broth* at 35 g./l. in deionized water.
*Trypticase soy broth is obtained from Difco Laboratories, Detroit, Mich.

The trypticase soy broth inoculum was incubated for 48 hours at a temperature of 30° C. After incubation, about 10 ml. of the inoculum was transferred to 500 ml. of the sterilized broth and was incubated for about 20 hours at 30° C. The pH was not adjusted. After incubation, the *Streptomyces granuloruber* No. A39912.13/pEL103 cells were ready for harvest and subsequent isolation of plasmid DNA.

B. Plasmid Isolation

About 12 g. (wet wgt) of *Streptomyces granuloruber* No. A39912.13/pEL103 cells were harvested by centrifugation (10 minutes, 4° C., 10,000 rpm). About 50 ml. of TES buffer (0.01M Tris(hydroxymethyl)aminoethane [tris], 0.001M EDTA, 34% sucrose, pH 8) was added to the cells followed by about 0.25 g. of lysozyme in 10 ml. of 0.25M EDTA. After the mixture was incubated at 37° C. for about 15 minutes, about 0.5 ml. of 10% Triton X-100 in TE buffer (0.01M Tris, 0.001M EDTA, pH 8) was added. The resultant mixture was then incubated at 65° C. for about 15 minutes. After the lysate was centrifuged (45 minutes, 4° C., 18,000 rpm), the supernatant was extracted four times with isoamyl alcohol and once with chloroform-isoamyl alcohol solution (24:1). Next about 0.5 ml. of 3M sodium acetate was added to the aqueous phase followed by 3 volumes of cold (−20° C.) 95% ethanol. The ethanol precipitation was rapidly performed in a dry ice-ethanol bath and the DNA precipitate was collected by centrifugation (15 minutes, 4° C., 10,000 rpm). The precipitate was vacuum dried and then resuspended in 1.1 ml. of STE buffer (0.01M Tris, 0.001M EDTA, 0.01M sodium chloride). Centrifugation (40 hours, 15° C., 35,000 rpm) using cesium chloride gradients, with ethidium bromide, was carried out to purify the plasmid DNA. Following centrifugation, the desired plasmid pEL103 DNA band was removed and the ethidium bromide extracted by conventional procedures. After precipitation of the DNA in 3 volumes of ethanol, the thus isolated plasmid pEL103 DNA was dissolved in 1 ml. of 10 fold diluted TE buffer and was then frozen at −20° C. for storage.

EXAMPLE 2

Construction of Plasmid pLR2

A. HindIII Digestion of Plasmid pIJ6

About 20 μl. (20 μg.) of plasmid pIJ6 DNA, disclosed in Thompson et al., 1980, Nature 286:525, 5 μl. BSA(-Bovine Serum albumin, 1 mg./ml.), 19 μl. water, 1 μl. of HindIII (containing 3 New England Bio Labs units) restriction enzyme*, and 5 μl. reaction mix** were incubated at 37° C. for 2 hours. The reaction was terminated by the addition of about 50 μl. of 4M ammonium acetate and 200 μl. of 95% ethanol. The resultant DNA precipitate was washed twice in 70% ethanol, dried in vacuo, suspended in 20 μl. of TE buffer, and frozen at −20° C. for storage.
*Restriction enzymes can be obtained from the following sources:

New England Bio Labs., Inc.
32 Tozer Road
Beverly, Mass. 01915

Boehringer-Mannheim Biochemicals
7941 Castleway Drive
Indianapolis, Ind. 46250

Bethesda Research Laboratories Inc.
P.O. Box 577
Gaithersburg, Md. 20760

**Reaction mix for HindIII restriction enzyme was prepared with the following composition.

600 mM NaCl
100 mM Tris-HCl, pH7.9
70 mM MgCl$_2$
10 mM Dithiothreitol

B. HindIII Digestion of Plasmid pBR322

About 8 μl. (4 μg.) of plasmid pBR322 DNA, 5 μl. reaction mix, 5 μl. BSA (1 mg./ml.), 31 μl. water, and 1 μl. of HindIII restriction enzyme were incubated at 37° C. for 2 hours. After the reaction was terminated by incubating at 60° C. for 10 minutes, about 50 μl. of ammonium acetate and 200 μl. of 95% ethanol were added. The resultant DNA precipitate was washed twice in 70% ethanol, dried in vacuo, and suspended in 45 μl. of water.

C. Ligation of HindIII Digested Plasmids pIJ6 and pBR322

About 20 μl. of HindIII treated plasmid pIJ6 (from Example 2A), 20 μl. of HindIII treated plasmid pBR322 (from Example 2B), 5 μl. BSA (1 mg./ml.), 1 μl. of T4 DNA ligase*, and 5 μl. ligation mix** were incubated at 16° C. for 4 hours. The reaction was terminated by the addition of about 50 μl. 4M ammonium acetate and 200 μl. of 95% ethanol. The resultant DNA precipitate was washed twice in 70% ethanol, dried in vacuo, and suspended in TE buffer. The suspended DNA constituted the desired plasmid pLR2.

*T4 DNA ligase can be obtained from the following source:

New England Bio Labs., Inc.
32 Tozer Rd.
Beverly, Mass. 01915

**Ligation mix was prepared with the following composition.

500 mM Tris-HCl, pH7.8
200 mM Dithiothreitol
100 mM MgCl₂
10 mM ATP

EXAMPLE 3

Construction of *E. coli* K12 HB101/pLR2

About 10 ml. of frozen competent *E. coli* K12 HB101 cells (Bolivar et al., 1977, Gene 2:75-93) were pelleted by centrifugation and then suspended in about 10 ml. of 0.01M sodium chloride. Next, the cells were pelleted again, resuspended in about 10 ml. of 0.03M calcium chloride, incubated on ice for 20 minutes, pelleted a third time, and finally, resuspended in 1.25 ml. of 0.03M calcium chloride. The resultant cell suspension was competent for subsequent transformation.

Plasmid pLR2 in TE buffer (prepared in Example 2C) was ethanol precipitated, suspended in 150 μl. of 30 mM calcium chloride solution, and gently mixed in a test tube with about 200 μl. of competent *E. coli* K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 μg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp®, Tet$^S$), and constituted the desired *E. coli* K12 HB101/pLR2 transformants.

EXAMPLE 4

Construction of Plasmid pLR1

Plasmid pLR1 was prepared in substantial accordance with the teaching of Example 2A-C except that plasmid pIJ2, disclosed in Thompson et al., 1980, Nature 286:525, was used in place of plasmid pIJ6. The desired plasmid pLR1 was suspended in TE buffer.

EXAMPLE 5

Construction of *E. coli* K12 HB101/pLR1

The desired construction was carried out in substantial accordance with the teaching of Example 3 except that plasmid pLR1, rather than plasmid pLR2, was used for transformation. Surviving colonies were selected and tested for the expected phenotype (Amp®, Tet$^S$), and constituted the desired *E. coli* K12 HB101/pLR1 transformants.

EXAMPLE 6

Construction of Plasmid pLR4

A. Partial BamHI Digestion of Plasmid pLR1

About 10 μl. (10 μg.) of plasmid pLR1, 5 μl. BSA (1 mg./ml.), 29 μl. water, 1 μl. of BamHI (diluted 1:4 with water) restriction enzyme, and 5 μl. reaction mix* were incubated at 37° C. for 15 minutes. The reaction was terminated by the addition of about 50 μl. of 4M ammonium acetate and 200 μl. of 95% ethanol. The resultant DNA precipitate was washed twice in 70% ethanol, dried in vacuo, and suspended in 20 μl. water.

*Reaction mix for BamHI restriction enzyme was prepared with the following composition.

1.5M NaCl
60 mM Tris-HCl, p$^H$7.9
60 mM MgCl₂

B. BamHI Digestion of Plasmid pBR322

The desired digestion was carried out in substantial accordance with the teaching of Example 2B except that BamHI restriction enzyme was used in place of HindIII restriction enzyme. The digested plasmid pBR322 was suspended in 29 μl. of water.

C. Ligation of Partial BamHI Digested Plasmid pLR1 and BamHI Digested Plasmid pBR322

The desired ligation was carried out in substantial accordance with the teaching of Example 2C. The resultant ligated DNA was suspended in TE buffer and constituted the desired plasmid pLR4.

EXAMPLE 7

Construction of *E. coli* K12 HB101/pLR4

The desired construction was carried out in substantial accordance with the teaching of Example 3 except that plasmid pLR4, rather than plasmid pLR2, was used for transformation. Surviving colonies were selected and tested for the expected phenotype (Amp®, Tet$^S$), and constituted the desired *E. coli* K12 HB101/pLR4 transformants.

EXAMPLE 8

Construction of Plasmids pEL107, pEL105, pEL108, and pEL104

A. BamHI Digestion of Plasmid pLR2 and Isolation of the 1.6 kb Thiostrepton Resistance-Conferring Fragment About 50 μg. of plasmid pLR2 DNA, 10 μl reaction mix, 10 μl. BSA (1 mg./ml.), 29 μl. water, and 1 μl. (4 units/μl.) of BamHI restriction enzyme were incubated at 37° C. for 2 hours. After adding an equal volume of 4M ammonium acetate and 2.5 volumes of 95% ethanol, the mixture was cooled at −20° C. for about 18 hours to precipitate the DNA. The DNA precipitate was collected by centrifugation and then suspended in about 50 μl. of TE buffer. The desired 1.6 kb BamHI restriction fragment was isolated conventionally from the DNA suspension by gel electrophoresis. Followng isolation, the fragment was resuspended in about 20 μl. of TE buffer for subsequent ligation.

B. Partial BamHI Digestion of Plasmid pEL103

About 20 μg. of plasmid pEL103 DNA, 10 μl. reaction mix, 10 μl. BSA (1 mg./ml.), 39 μl. water, and 1 μl. of BamHI restriction enzyme (prepared by diluting 2 μl. of enzyme in 8 μl. of water) were incubated at ambient temperature for about 15 minutes. After adding an equal volume of 4M ammonium acetate and 5 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 50 μl. of TE buffer.

C. Ligation

A mixture of about 20 μg. of the partially digested plasmid pEL103 DNA, 10 μg. of the 1.6 kb BamHI restriction fragment of plasmid pLR2, 5 μl. ligation mix, 5 μl. BSA (1 mg./ml.), 10 μl. water, and 1 μl. T4 DNA ligase were incubated at about 16° C. for about 4 hours. After adding 40 μl. of 4M ammonium acetate and 200 μl. of cold ethanol, the mixture was cooled to −20° C. for about 18 hours to precipitate the DNA. The DNA precipitate was collected by centrifugation, washed with 70% ethanol, collected again, and then suspended in 50 μl. of medium P (Hopwood and Wright 1978, J. Molecular and General Genetics 162:307) for subsequent transformation.

Figure 5:
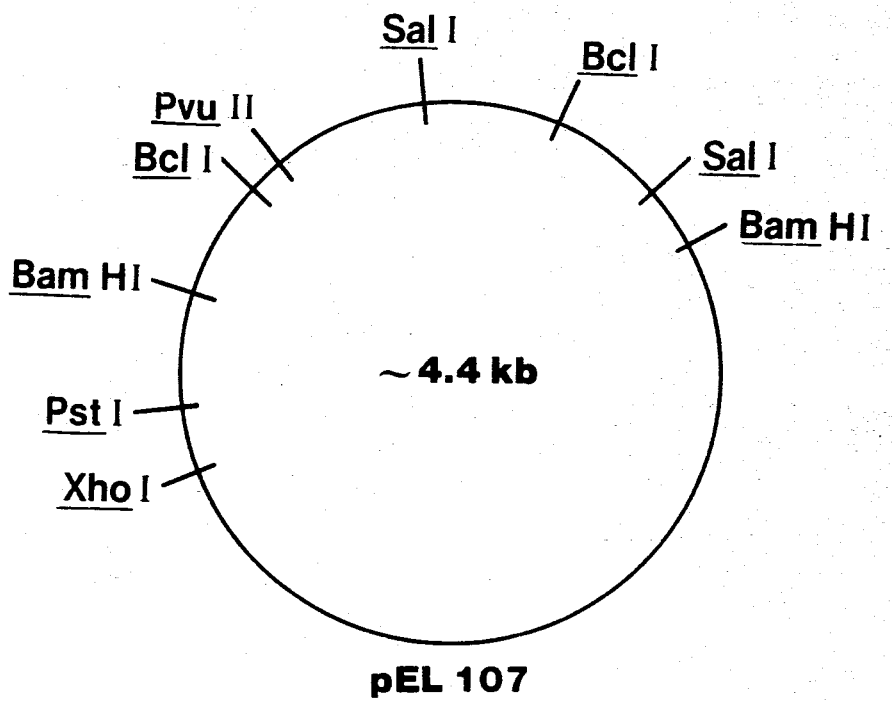
Figure 5:
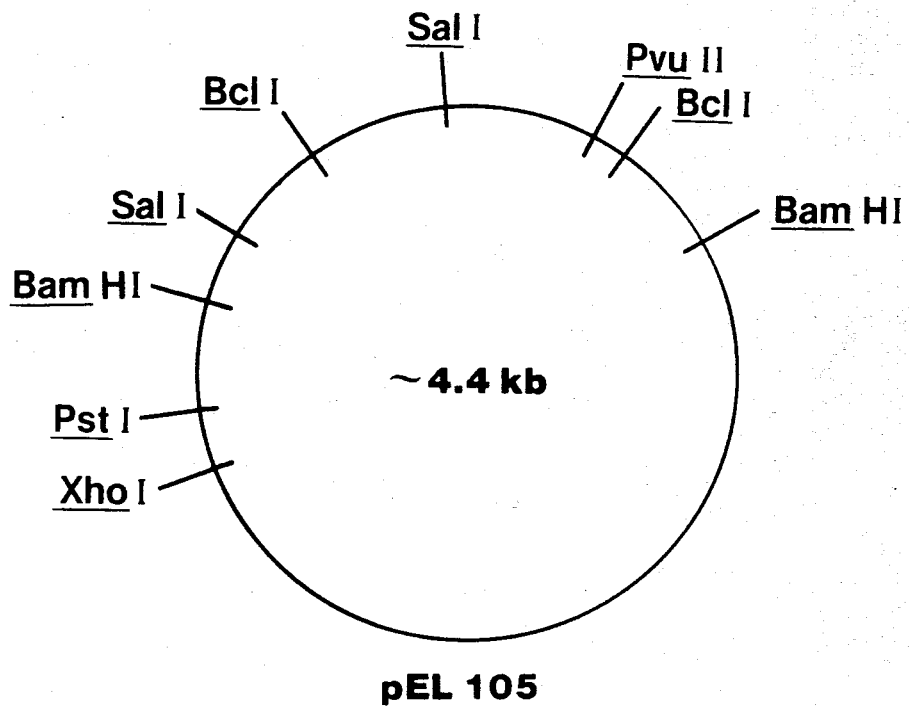
Figure 6:
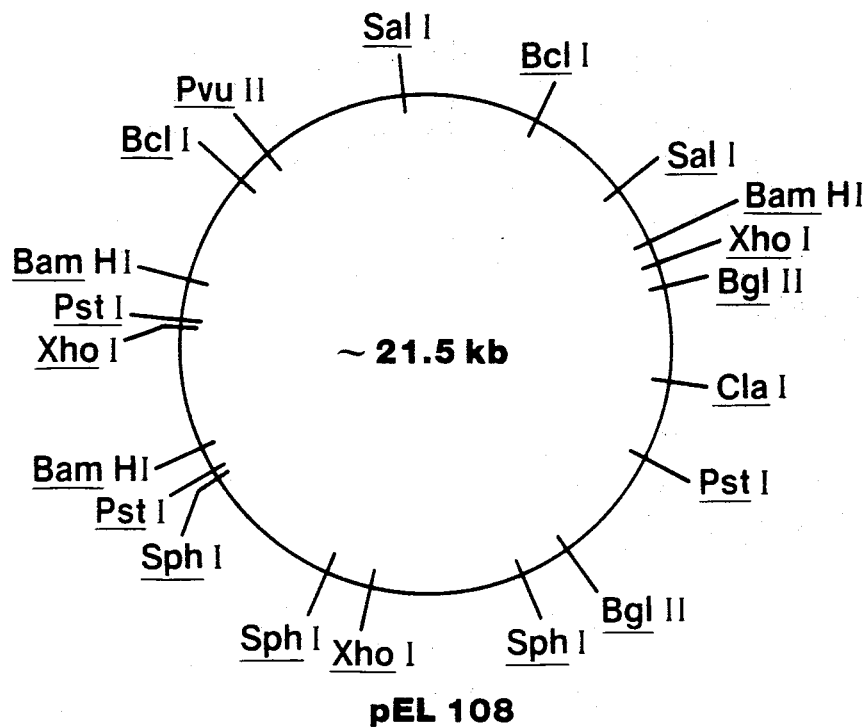
Figure 6:
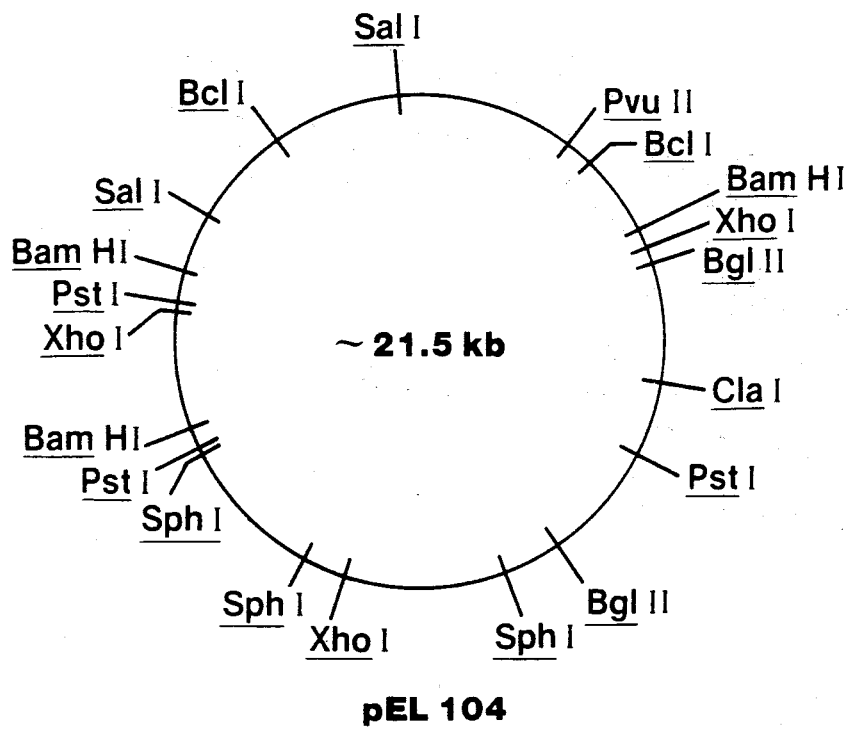

Recombinant plasmids of at least two types result depending upon which of the possible pEL103 restriction fragments becomes ligated to the 1.6 kb BamHI thiostrepton resistance-conferring fragment. Thus, ligation to the 2.8 kb BamHI restriction fragment of plasmid pEL103 results in the 4.4 kb plasmids pEL107 and pEL105 and ligation to the 19.9 kb BamHI fragment (linearized pEL103) results in the 21.5 kb plasmids pEL108 and pEL104. In addition, the insertional isomers of plasmids pEL108 and pEL104 are also produced since plasmid pEL103 has there BamHI restriction sites for the insertion of the thiostrepton resistance fragment. Recombinant plasmids of two orientations result because the 1.6 kb BamHI resistance-conferring fragment can be oriented in either direction. A restriction site and functional map of each of plasmids pEL107 and pEL105, and plasmids pEL108 and pEL104, is presented respectively in FIGS. 5 and 6 of the accompanying drawings.

Those skilled in the art will recognize and understand that the partial BamHI digestion of plasmid pEL103 produces a mixture of different restriction fragments that can be ligated with each other and also with one or more resistance-conferring DNA fragments to produce several additional recombinant plasmids. Any additional plasmids that contain the 2.8 kb BamHI origin of replication-containing fragment are functional and thus further exemplify the present invention. The aforementioned additional plasmids can be conventionally transformed into appropriate host cells and then identified by restriction enzyme and gel electrophoretic analysis.

EXAMPLE 9

Construction of *Streptomyces ambofacien*/pEL107, *S. ambofaciens*/pEL105, *S. ambofacien*/pEL108, and *S. ambofaciens*/pEL104

Using about 20 μg. of the DNA from Example 8C and 1×10⁹ protoplasts of *Streptomyces ambofaciens*, a strain deposited and made part of the permanent stock culture collection of the Northern Regional Research Laboratory, Peoria, Ill., from which it is available to the public under the accession number NRRL 2420, the desired constructions were made in substantial accordance with the teaching of International Publication (of International Patent Application No. PCT/GB79/00095) No. WO79/01169, Example 2. The desired transformants were selected for thiostrepton resistance by overlaying the regenerating protoplasts with R2 medium (Hopwood and Wright, 1978, Molecular and General Genetics 162:30) top agar containing sufficient thiostrepton to bring the final plate concentration to 50 μg./ml. The resultant *Streptomyces ambofaciens*/pEL107, *S. ambofaciens*/pEL105, *S. ambofaciens*/pEL108, and *S. ambofaciens*/pEL104 thiostrepton resistant colonies were isolated according to known procedures, cultured, and then conventionally identified by restriction enzyme and electrophoretic analysis of the constitutive plasmids.

EXAMPLE 10

Construction of Plasmids pEL109, pEL110, pEL111, and pEL112

A. BamHI Digestion of Plasmid pLR1 and Isolation of the 3.4 kb Neomycin Resistance Conferring Fragment The desired digestion and isolation are carried out in substantial accordance with the teaching of Example 8A. The 3.4 kb BamHI restriction fragment is suspended in about 20 μl. of TE buffer for subsequent ligation.

B. Ligation

The 3.4 kb BamHI neomycin resistance conferring restriction fragment is ligated to partially BamHI digested plasmid pEL103 (prepared in Example 8B) in substantial accordance with the teaching of Example 8C.

Figure 7:
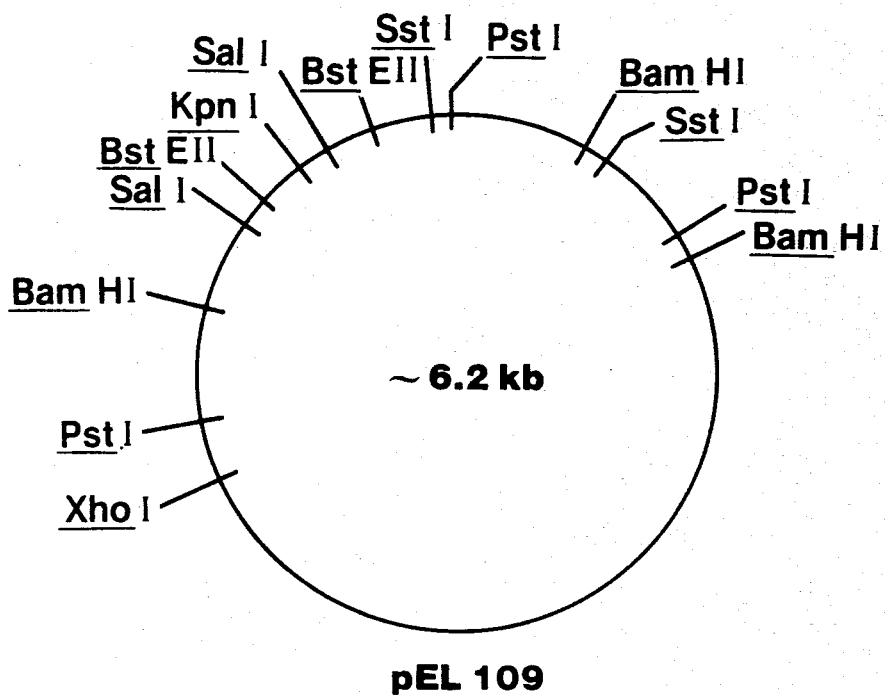
Figure 7:
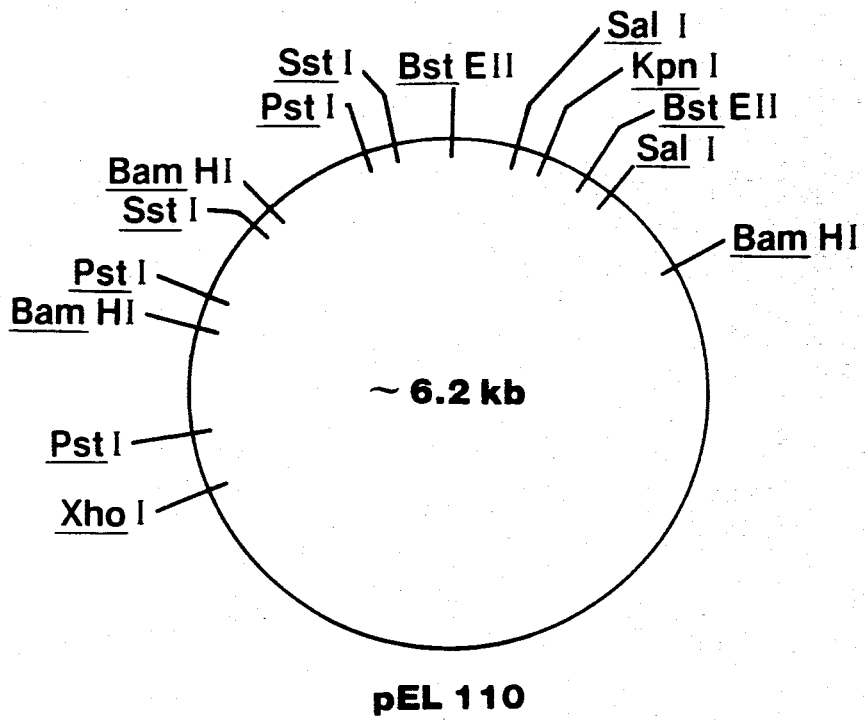
Figure 8:
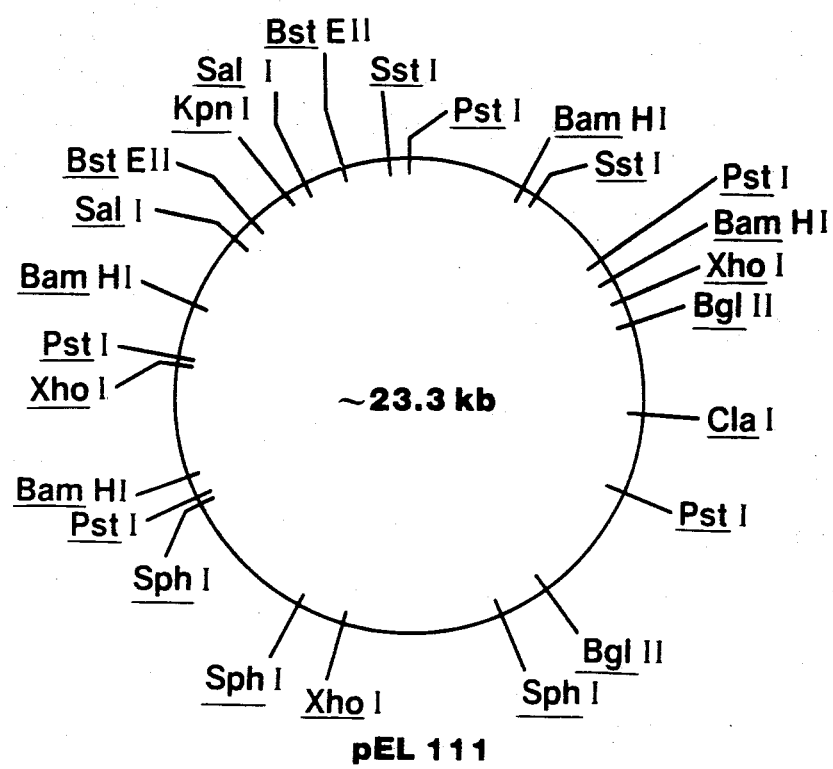
Figure 8:
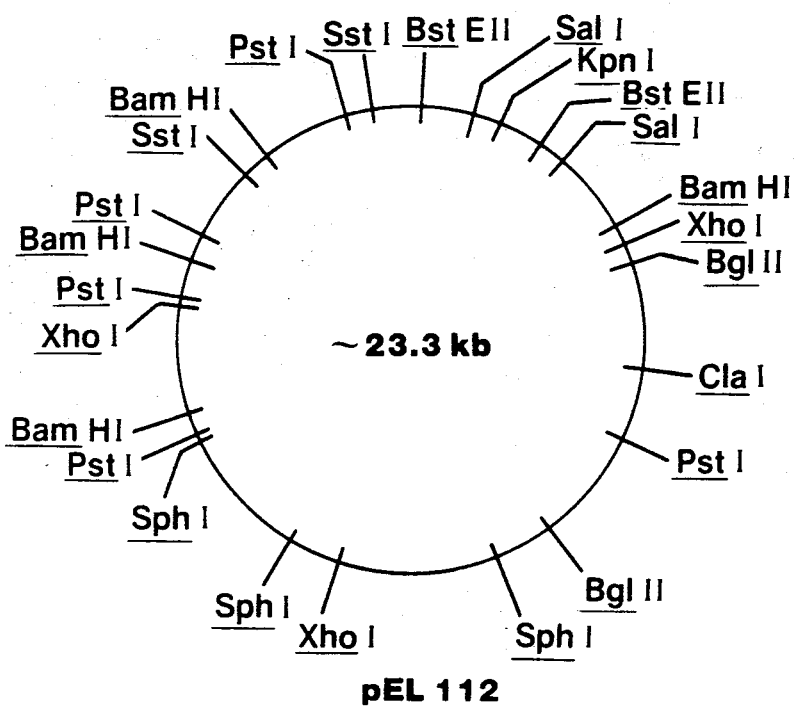

Recombinant plasmids of at least two types result depending upon which of the possible pEL103 restriction fragments becomes ligated to the 3.4 kb BamHI neomycin resistance-conferring fragment. Thus, ligation to the 2.8 kb BamHI restriction fragment of plasmid pEL103 results in the 6.2 kb plasmids pEL109 and pEL110 and ligation to the 19.9 kb BamHI fragment (linearized pEL103) results in the 23.3 kb plasmids pEL111 and pEL112. In addition, the insertional isomers of plasmids pEL111 and pEL112 are also produced since plasmid pEL103 has three BamHI restriction sites for the insertion of the neomycin resistance fragment. Recombinant plasmids of two orientations result because the 3.4 kb BamHI resistance-conferring fragment can be oriented in either direction. A restriction site and functional map of each of plasmids pEL109 and pEL110, and plasmids pEL111 and pEL112, is presented respectively in FIGS. 7 and 8 of the accompanying drawings.

Those skilled in the art will recognize and understand, as described in Example 8C, that additional recombinant plasmids containing the 2.8 kb BamHI origin of replication-containing fragment can be generated by the above procedure. These plasmids are functional and thus further exemplify the present invention. The aforementioned additional plasmids can be conventionally transformed and then identified by restriction enzyme and gel electrophoretic analysis.

EXAMPLE 11

Construction of *Streptomyces ambofaciens*/pEL109 *S. ambofaciens*/pEL110, *S. ambofaciens*/pEL111, and *S. ambofaciens*/pEL112

Using about 20 μg. of the DNA from Example 10 and 1×10⁸ protoplasts of *Streptomyces ambofaciens* (NRRL No. 2420), the desired constructions are made in substantial accordance with the teaching of International Publication (of International Patent Application No. PCT/GB79/00095) No. WO79/01169, Example 2. The desired transformants are selected for neomycin resistance by overlaying the regenerating protoplasts with R2 medium top agar containing sufficient neomycin* to bring the final plate concentration to 1 μg./ml.
*Antibiotic neomycin can be obtained from Sigma, St. Louis, Mo.

The resultant *Streptomyces ambofaciens/*-pEL109, *S. ambofaciens*/pEL110, *S. ambofaciens*/pEL111, and *S. ambofaciens*/pEL112 neomycin resistant colonies are isolated according to known procedures and then conventionally identified by restriction enzyme and electrophoretic analysis of the constitutive plasmids.

EXAMPLE 12

Construction of Plasmids pEL113 and pEL114

Figure 9:
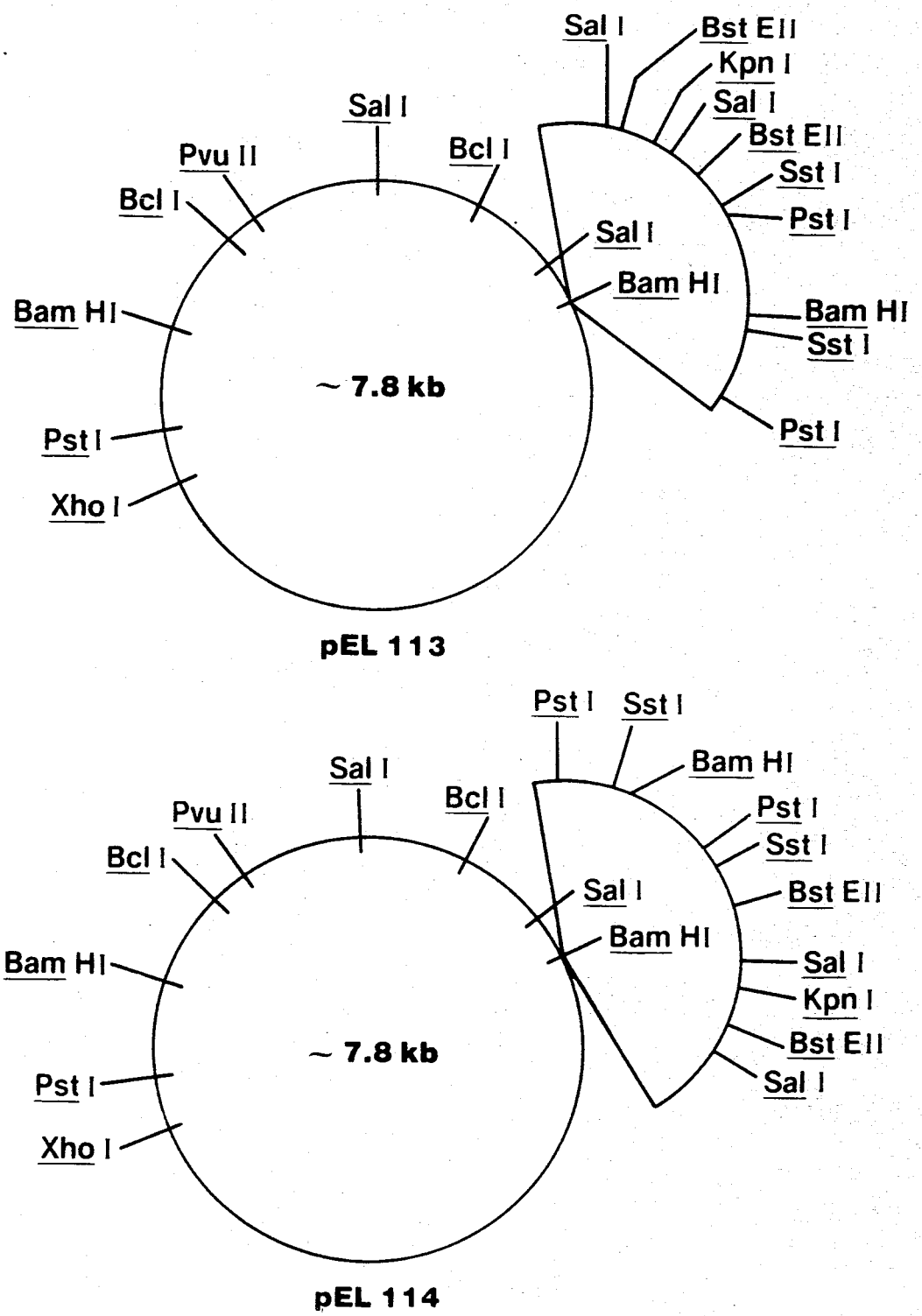

Plasmid pEL107 is isolated from *Streptomyces ambofaciens*/pEL107 (prepared in Example 9) according to the procedure of Example 1 and then is partially digested with BamHI restriction enzyme in substantial accordance with the teaching of Example 8B. The partial BamHI digest is then ligated, in substantial accordance with the teaching of Example 8C, with the 3.4 kb neomycin resistance-conferring BamHI fragment (prepared in Example 10A) of plasmid pLR1 to produce the desired plasmids. The insertional isomers of plasmids pEL113 and pEL114 are also produced since plasmid pEL107 has two BamHI restriction sites for the insertion of the neomycin resistance fragment. Recombinant plasmids of two orientations result because the 3.4 kb BamHI neomycin resistance-conferring fragment can be oriented in either direction. A restriction site and functional map of each of plasmids pEL113 and pEL114 is presented in FIG. 9 of the accompanying drawings.

EXAMPLE 13

Construction of *Streptomyces ambofaciens*/pEL113 and *S. ambofaciens*/pEL114

Using 20 μg. of the DNA from Example 12 and $1 \times 10^8$ protoplasts of *Streptomyces ambofaciens* (NRRL No. 2420), the desired constructions are made in substantial accordance with the teaching of International Publication (of International Patent Application No. PCT/GB79/00095) No. WO79/01169, Example 2. The desired transformants are selected first for thiostrepton resistance and then for neomycin resistance by the methods described in Examples 9 and 11 above. The resultant *Streptomyces ambofaciens*/pEL113 and *S. ambofaciens*/pEL114 thiostrepton and neomycin resistant colonies are isolated according to known procedures and then conventionally identified by restriction enzyme and electrophoretic analysis of the constitutive plasmids.

EXAMPLE 14

Construction of Plasmids pEL115 and pEL116

Figure 10:
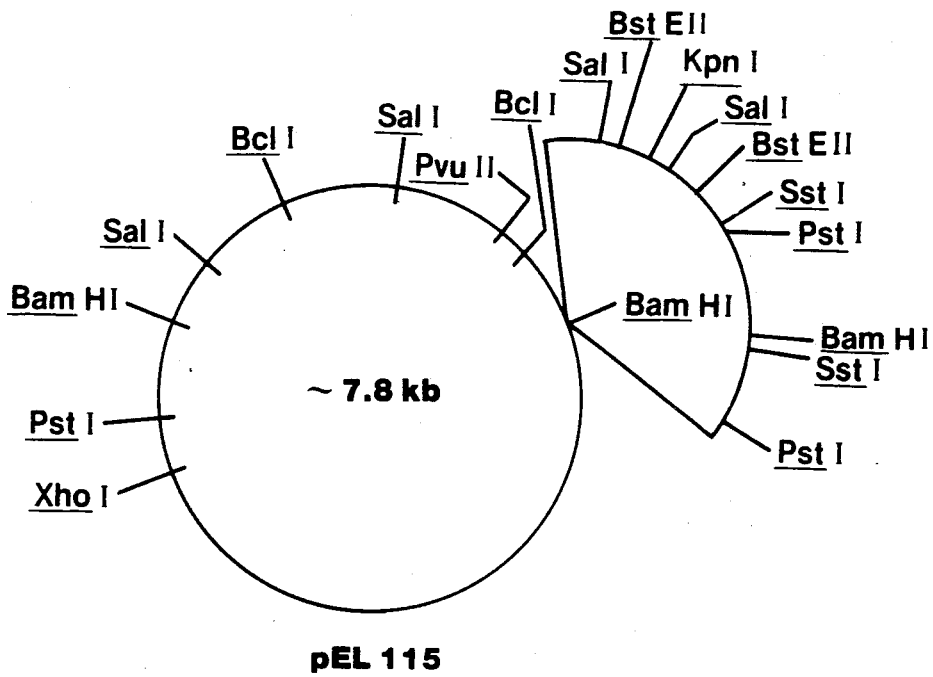
Figure 10:
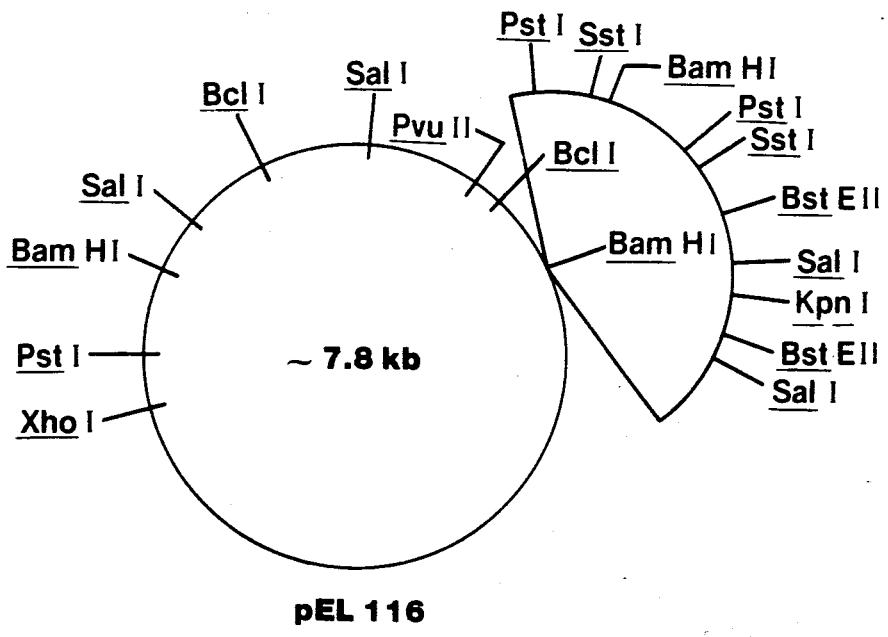

The desired plasmids are constructed in substantial accordance with the teaching of Example 12 with the exception that plasmid pEL105, rather than plasmid pEL107, is used in the partial BamHI digestion. The insertional isomers of plasmids pEL115 and pEL116 are also produced since plasmid pEL105 has two BaMHI restriction sites for the insertion of the neomycin resistance fragment. Recombinant plasmids of two orientations result because the 3.4 kb BamHI neomycin resistance-conferring fragment can be oriented in either direction. A restriction site and functional map of each of plasmids pEL115 and pEL116 is presented in FIG. 10 of the accompanying drawings.

EXAMPLE 15

Construction of *Streptomyces ambofaciens*/pEL115 and *S. ambofaciens*/pEL116

Using 20 μg. of the DNA from Example 14, the desired constructions are made in substantial accordance with the teaching of Example 13. The resultant *Streptomyces ambofaciens*/pEL115 and *S. ambofaciens*/pEL116 thiostrepton and neomycin resistant colonies are isolated according to known procedures and then conventionally identified by restriction enzyme and electrophoretic analysis of the constitutive plasmids.

EXAMPLE 16

Construction of Plasmids pEL117 and pEL118 and plasmids pEL119 and pEL120

Figure 11:
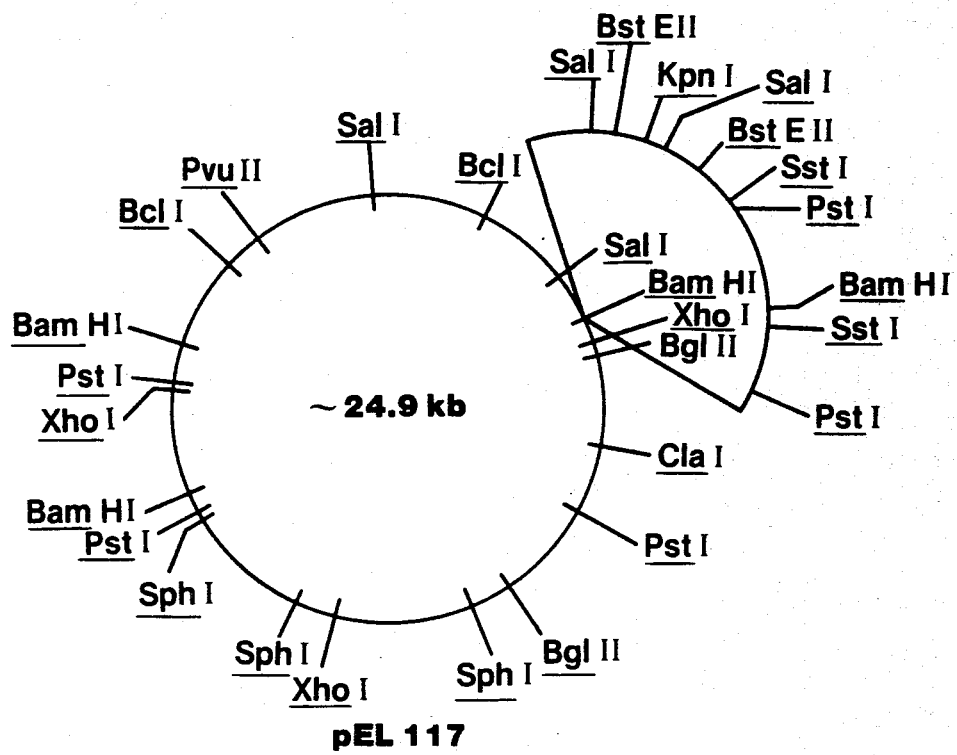
Figure 11:
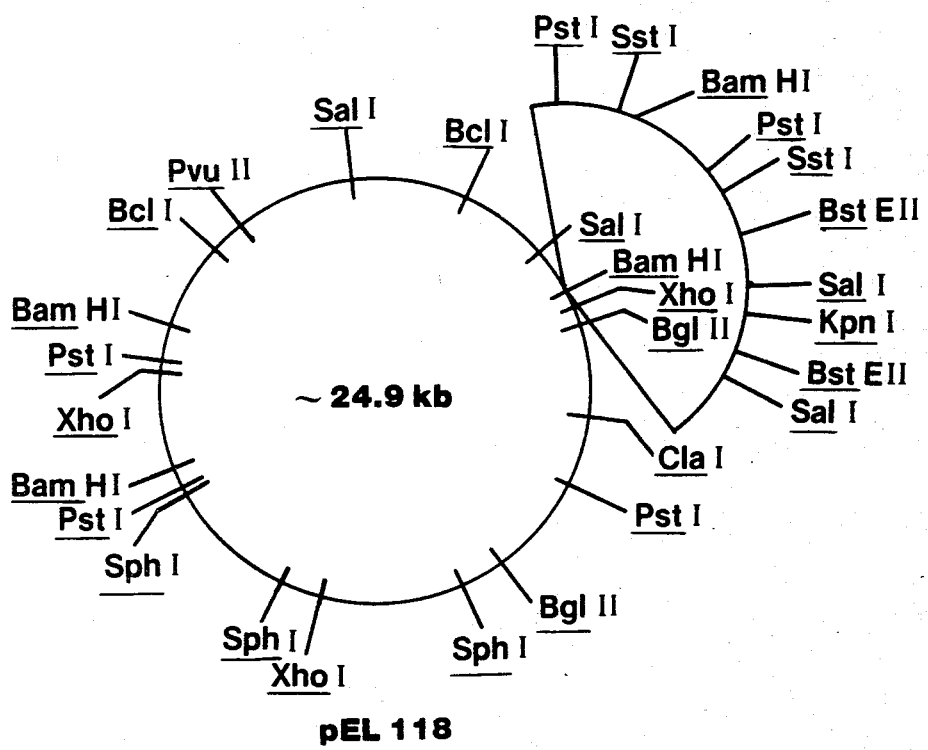
Figure 12:
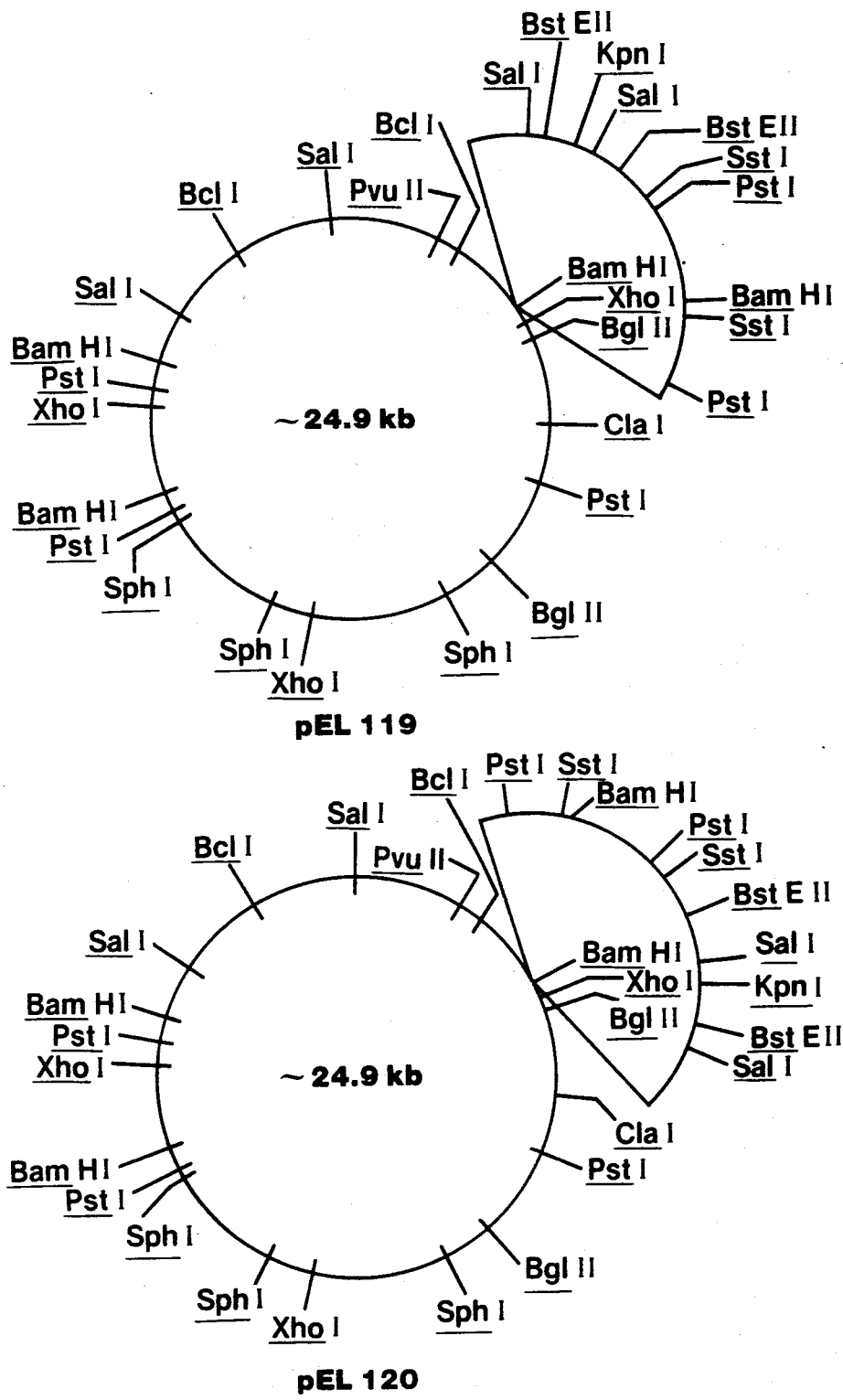

The desired plasmids are respectively constructed in substantial accordance with the teachings of Examples 12 and 14 with the exception that plasmids pEL108 and pEL104, rather than plasmids pEL107 and pEL105 are respectively used in the partial BamHI digestions. In addition, the insertional isomers of plasmids pEL117, pEL118, pEL119, and pEL120 are also produced since plasmids pEL108 and pEL104 contain three BamHI restriction sites for the insertion of the neomycin resistance fragment. Recombinant plasmids of two orientations result because the 3.4 kb BamHI neomycin resistance-conferring fragment can be oriented in either direction. A restriction site and functional map of each of plasmids pEL117 and pEL118, and plasmids pEL119 and pEL120, is presented respectively in FIGS. 11 and 12 of the accompanying drawings.

EXAMPLE 17

Construction of *Streptomyces ambofacines*/pEL117 and *S. ambofaciens*/pEL118 and *Streptomyces ambofaciens*/pEL119, and *S. ambofaciens*/pEL120

About 20 μg. of the plasmid pEL117, pEL118, pEL119, and pEL120 DNA mixture of Example 16 are respectively transformed into *Streptomyces ambofaciens* in substantial accordance with the teachings of Examples 13 and 15. The resultant *Streptomyces ambofaciens*/pEL117, *S. ambofaciens*/pEL118, *S. ambofaciens*/pEL119, and *S. ambofaciens*/pEL120 thiostrepton and neomycin resistant colonies are isolated according to known procedures and then conventionally identified by restriction enzyme and electrophoretic analysis of the constitutive plasmids.

EXAMPLE 18

Construction of Chimeric Plasmids pEL121 and pEL122

Figure 13:
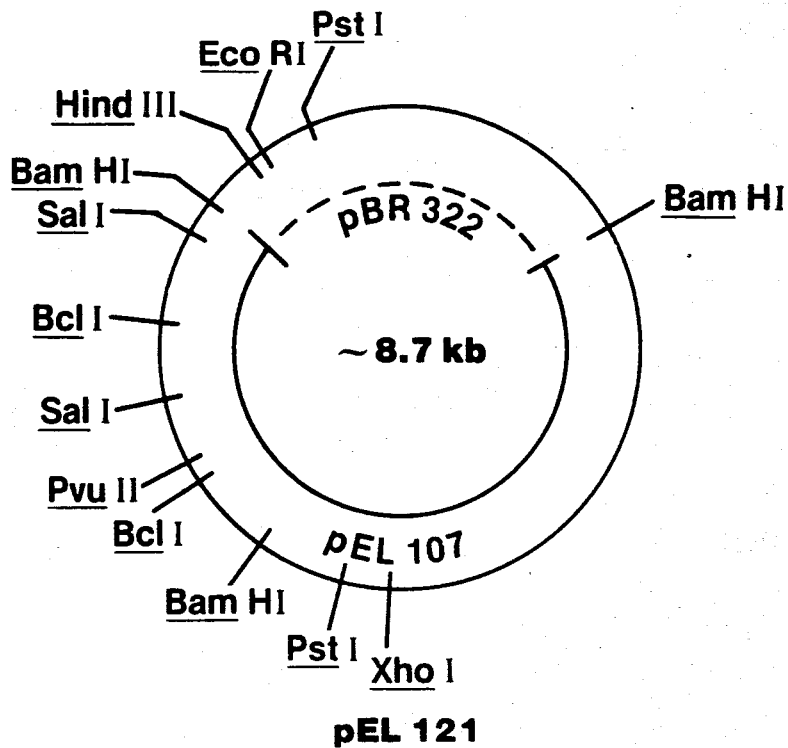
Figure 13:
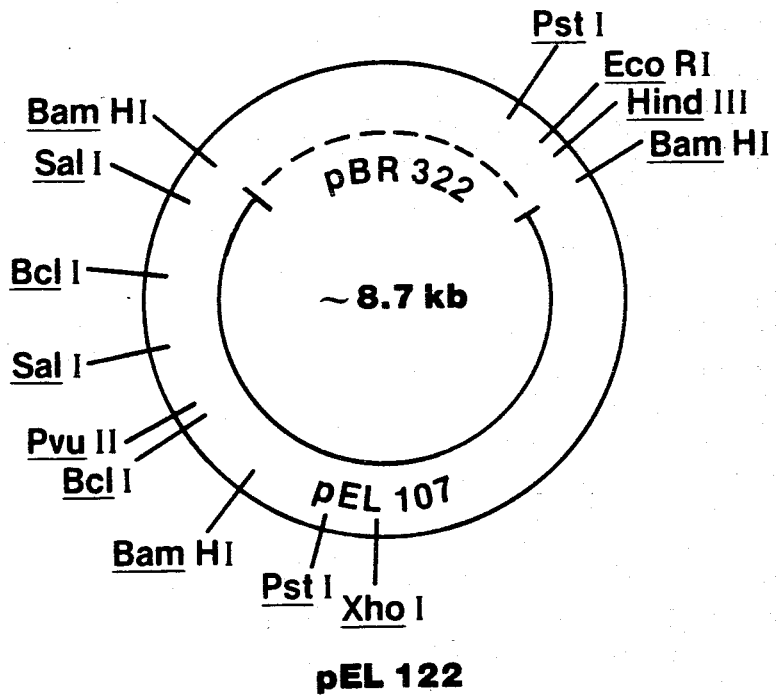

The desired chimeric plasmids are obtained by ligating a partial BamHI digest of plasmid pEL107 onto BamHI digested plasmid pBR322 in substantial accordance with the ligation procedure of Example 8C. Plasmid pEL107 is isolated from *Streptomyces ambofaciens*/pEL107 (prepared in Example 9) in substantial accordance with the teaching of Example 1 and then partially BamHI digested according to the procedure of Example 8B. The BamHI digested plasmid pBR322 is prepared in substantial accordance with the procedure of Example 2B with the exception that BamHI, rather than HindIII, restriction enzyme is used. The desired chimeric plasmid DNA is collected by centrifugation, washed with 70% ethanol, dried in vacuo, and then suspended in 50 μl. of TE buffer. In addition, the insertional isomers of plasmids pEL121 and pEL122 are also produced since plasmid pEL107 has two BamHI restriction sites for the insertion of the restricted plasmid pBR322. Recombinant plasmids of two orientations result because the restricted plasmid pBR322 can be oriented in either direction. A restriction site and functional map of each of plasmids pEL121 and pEL122 is presented in FIG. 13 of the accompanying drawings.

EXAMPLE 19

Construction of *E. coli* K12 HB101/pEL121 and *E. coli* K12 HB101/pEL122

The desired constructions are made in substantial accordance with the teaching of Example 3 with the exception that plasmids pEL121 and pEL122, rather than plasmid pLR2, are used for the transformation. Surviving colonies are first selected, and tested for the expected phenotype (Amp$^R$, Tet$^S$), and then conventionally identified as the desired *E. coli* K12 HB101/pEL121 and *E. coli* K12 HB101/pEL122 transformants by restriction enzyme and gel electrophoretic analysis of the constitutive plasmids.

EXAMPLE 20

Construction of *Streptomyces ambofaciens*/pEL121 and *S. ambofaciens*/pEL122

The desired constructions are made in substantial accordance with the teaching of Example 9 with exception that plasmids pEL121 and pEL122, rather than plasmids pEL107, pEL105, pEL108, and pEL104, are used for the transformation. The resulting transformants are selected for thiostrepton resistance by the method described in Example 9 above. The thus constructed thiostrepton resistant *Streptomyces ambofaciens*/pEL121 and *S. ambofaciens*/pEL122 colonies are isolated according to known procedures and then conventionally identified by restriction enzyme and electrophoretic analysis of the constitutive plasmids.

EXAMPLE 21

Construction of Plasmid pFJ124

A. BamHI (Partial) and BclI Digestion of Plasmid pEL105

About 20 μg. of plasmid pEL105 DNA, 10 μl. reaction mix, 10 μl. BSA (1 mg./ml.) 39 μl. water, and 1 μl. of BamHI restriction enzyme (prepared by diluting 2 μl. of enzyme in 8 μl. of water) were incubated at ambient temperature for about 15 minutes. After adding an equal volume of 4M ammonium acetate and 2 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 20 μl. of TE buffer. Following addition of about 5 μl. of BclI reaction mix*, 10 μl. BSA (1 mg./ml.), 39 μl. water, and 1 μl. of BclI restriction (containing excess New England Bio Lab units), the mixture was incubated at 50° C. for about 60 minutes. An equal volume of 4M ammonium acetate and 5 volumes of 95% ethanol were added and then the mixture was cooled at −20° C. for about 18 hours to precipitate the DNA. The DNA precipitate was collected by centrifugation, rinsed in 70% ethanol, dried in vacuo, and then suspended in about 50 μl. of TE buffer.

*Reaction mix for BclI restriction enzyme was prepared with the following composition.

750 mM KCl
60 mM Tris-HCl, pH 7.4
100 mM MgCl$_2$
10 mM Dithiothreitol

B. Ligation

A mixture of about 20 μg. of the partially digested plasmid pEL105 DNA, 5 μl. ligation mix, 5 μl. BSA (1 mg./ml.), 10 μl. water, and 1 μl. T4 DNA ligase were incubated at about 16° C. for about 4 hours. After adding 40 μl. of 4M ammonium acetate and 200 μl. of cold ethanol, the mixture was cooled to −20° C. for about 18 hours to precipitate the DNA. The DNA precipitate was collected by centrifugation, washed with 70% ethanol, collected again, and then suspended in 50 μl. of medium P for subsequent transformation.

Those skilled in the art will understand that the partial BamHI and BclI digestion of plasmid pEL105 produces a mixture of fragments that can be self ligated or ligated to each other to produce several additional plasmids. The desired plasmid pFJ124, along with the aforementioned additional plasmids, can be transformed into appropriate host cells and then conventionally identified by restriction enzyme and gel electrophoretic analysis.

EXAMPLE 22

Construction of *Streptomyces ambofaciens*/pFJ124

Figure 14:
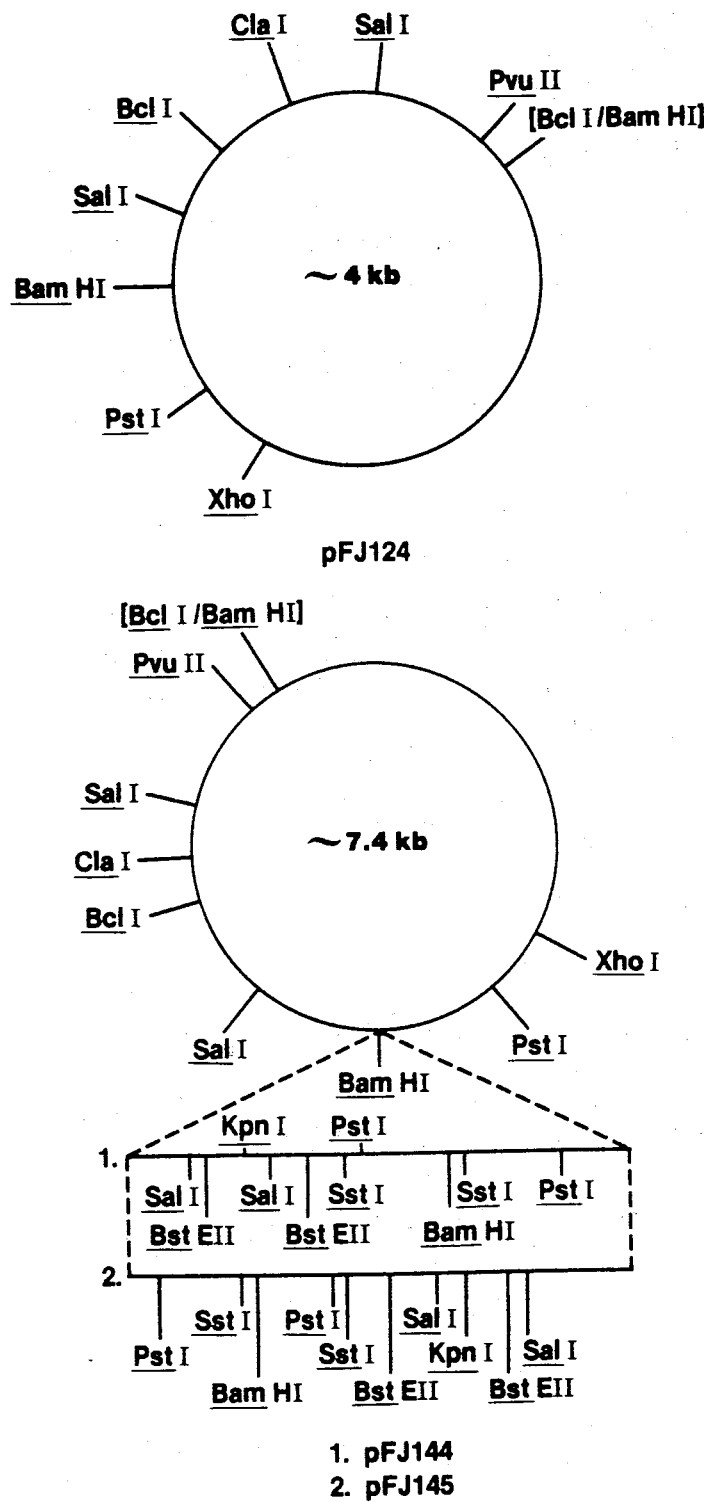

The desired construction was made in substantial accordance with the teaching of Example 9 except that DNA from Example 21, rather than Example 8C, was used. The resultant thiostrepton resistant transformant colonies were isolated according to known procedures, cultured, and then conventionally identified by restriction enzyme and electrophoretic analysis of the constitutive plasmids. The desired *Streptomyces ambofaciens*/pFJ124 transformants were then cultured for subsequent production and isolation of plasmid pFJ124 according to known procedures. A restriction site map of the ~4.0 kb plasmid pFJ124 is presented in FIG. 14 of the accompanying drawings.

EXAMPLE 23

Construction of Plasmids pFJ144 and pFJ145

A. BamHI Digestion of Plasmid pFJ124

The digestion is carried out in substantial accordance with the teaching of Example 8A except that plasmid pFJ124, rather than plasmid pLR2, is used. The DNA precipitate is suspended in about 50 μl. of TE buffer and constitutes the desired BamHI digest.

B. Ligation

The 3.4 kb BamHI neomycin resistance-conferring restriction fragment (prepared in Example 10A), is ligated to BamHI digested plasmid pFJ124 in substantial accordance with the teaching of Example 8C. Recombinant plasmids of two orientations result because the 3.4 kb BamHI resistance-conferring fragment can be oriented in either direction. Plasmids pFJ144 and pFJ145 can be conventionally transformed into appropriate host cells and then identified by restriction enzyme and gel electrophoretic analysis.

EXAMPLE 24

Construction of *Streptomyces ambofaciens*/pFJ144 and *S. ambofaciens*/pFJ145

The desired constructions are made in substantial accordance with the teaching of Example 11 except that DNA from Example 23, rather than Example 10, is used. The resultant *Streptomyces ambofaciens/-*pFJ144 and *S. ambofaciens*/pFJ145 neomycin resistant colonies are isolated according to known procedures, cultured, tested for thiostrepton resistance, and then conventionally identified by restriction enzyme and gel electrophoretic analysis of the constitutive plasmids. The transformants are then conventionally cultured for subsequent production and isolation of plasmids pFJ144 and pFJ145. A restriction site map of each of the ~7.4 kb plasmids pFJ144 and pFJ145 is presented in FIG. 14 of the accompanying drawings.

EXAMPLE 25

Construction of Plasmid pFJ146

Figure 15:
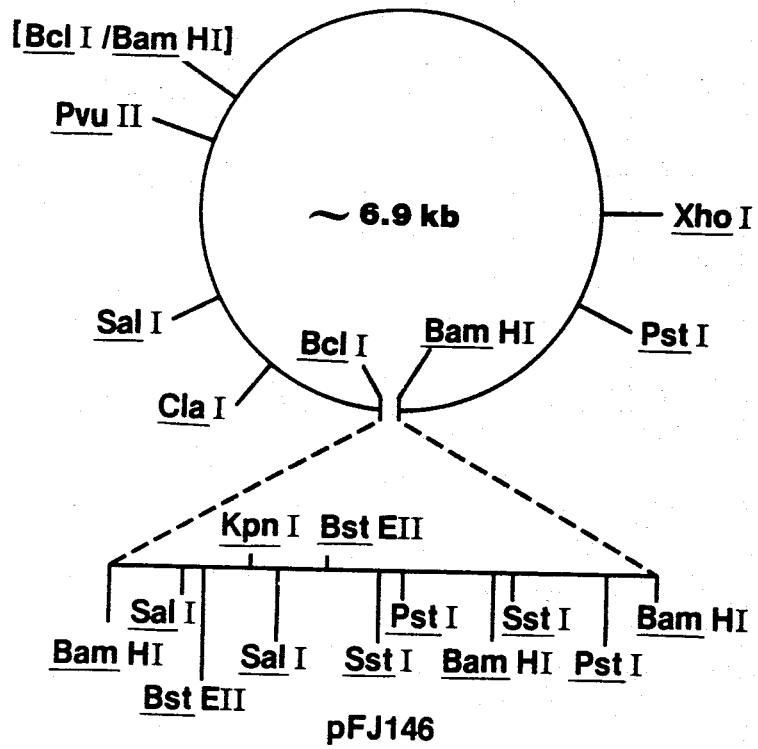
Figure 15:
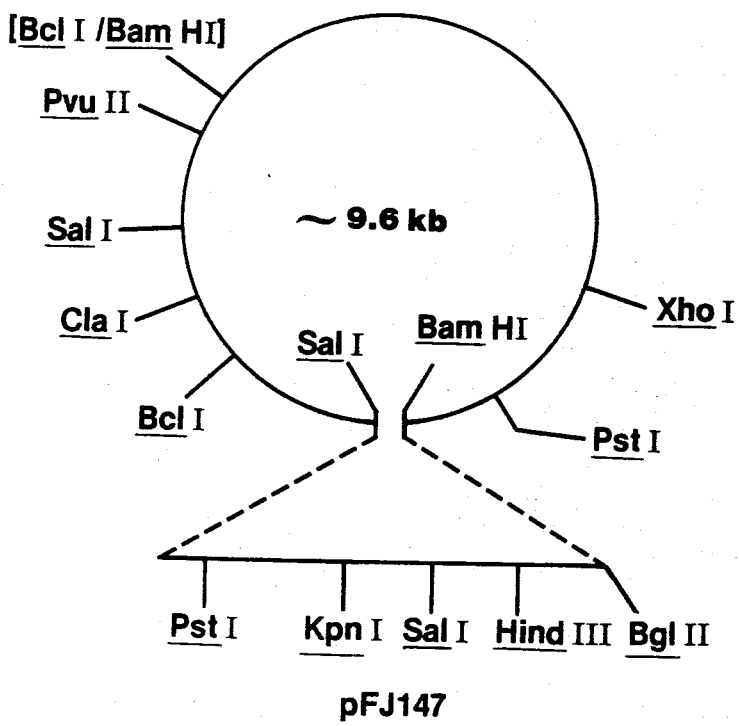

The desired construction is made in substantial accordance with the teaching of Example 21 except that both digestions are partial and plasmid pFJ144, rather than plasmid pEL105, is used. The resultant DNA precipitate is collected by centrifugation, washed with 70% ethanol, collected again, and then suspended in 50 μl. of medium P for subsequent transformation. A restriction site map of plasmid pFJ146 is presented in FIG. 15 of the accompanying drawings.

EXAMPLE 26

Construction of *Streptomyces ambofaciens*/pFJ146

The desired construction is made in substantial accordance with the teaching of Example 11 except that plasmid pFJ146, rather than DNA from Example 10, is used.

EXAMPLE 27

Construction of Plasmid pFJ147

A. Culture of *E. coli* 803/pIJ43 and Isolation of Plasmid pIJ43

The desired culturing of *E. coli* 803/pIJ43 (ATCC 39156) and the subsequent isolation of plasmid pIJ43 are both carried out in substantial accordance with the teaching of Davis, R. W. et al., 1980, A Manual For Genetic Engineering, Advanced Bacterial Genetics, Cold Spring Harbor Laboratory, Cold Spring Harbor, N.Y. The pIJ43 DNA is conventionally suspended in TE buffer and then cooled to −20° C. for storage.

B. Digestion and Isolation of ~2.7 kb SalI-BglII Fragment of Plasmid pIJ43

The desired digestion is carried out in substantial accordance with the teaching of Example 21 except that plasmid pIJ43, SalI restriction enzyme and reaction mix*, and BglII restriction enzyme and reaction mix**, rather than plasmid pEL105, BamHI restriction enzyme and reaction mix, and BclI restriction enzyme and reaction mix, were used. In addition, the SalI digestion was partial. The resultant SalI-BglII fragments were separated and isolated conventionally by agarose gel electrophoresis (Davis, R. W. et al., 1980).

C. BamHI and Partial SalI Digestion of Plasmid pFJ124

About 20 μg. of plasmid pFJ124 DNA, 10 μl. BSA (1 mg./ml.), 39 μl. water, 1 μl. of BamHI restriction enzyme (containing excess New England Bio Lab units), and 10 μl. reaction mix were incubated at 37° C. for 60 minutes. The mixture was then incubated at 65° C. for 10 minutes, cooled to 4° C., supplemented with 10 μl. of SalI reaction mix* and 1 μl. of SalI restriction enzyme (containing excess New England Bio Lab units), and then incubated again at 37° C. for about 60 minutes. After adding an equal volume of 4M ammonium acetate and 2 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 50 μl. of TE buffer.

*Reaction mix for SalI restriction enzyme was prepared with the following composition.

1.5M NaCl
60 mM Tris-HCl, pH7.9
60 mM MgCl₂
60 mM β-mercaptoethanol
1 mg./ml. BSA

**Reaction mix for BGlII restriction enzyme was prepared with the following composition.

0.6M NaCl
100 mM Tris-HCl, pH7.4
100 mM MgCl₂
100 mM β-mercaptoethanol
1 mg./ml. BSA D. Ligation The ~2.7 kb SalI-BglII fragment of plasmid pIJ43 was ligated to the BamHI-partial SalI digest of plasmid pFJ124 in substantial accordance with the teaching of Example 8C. The resultant DNA precipitate was collected by centrifugation, washed with 70% ethanol, collected again, and then suspended in 50 μl. of medium P for subsequent transformation. A restriction site map of plasmid pFJ147 is presented in FIG. 15 of the accompanying drawings.

EXAMPLE 28

Construction of *Streptomyces ambofaciens*/pFJ147

The desired construction was made in substantial accordance with the teaching of Example 9 except that plasmid pFJ147 (prepared in Example 27), rather than DNA from Example 8C, was used. The desired transformants were selected for erythromycin resistance by overlaying the regenerating protoplasts with R2 medium top agar containing sufficient erythromycin to bring the plate concentration to 50 μg./ml. The resultant erythromycin resistant colonies were tested for thiostrepton resistance and constituted the desired *Streptomyces ambofaciens*/pFJ147 transformants. The identity was further confirmed conventionally by restriction enzyme and gel electrophoretic analysis of the constitutive plasmid.

EXAMPLE 29

Construction of Plasmids pFJ148 and pFJ149

A. Partial SalI Digestion of Plasmid pIJ43

The desired digestion was carried out in substantial accordance with the teaching of Example 6 except that plasmid pIJ43 and SalI restriction enzyme and reaction mix, rather than plasmid pLR1 and BamHI restriction enzyme and reaction mix, were used. The resultant partial SalI fragments were separated and isolated conventionally by agarose gel electrophoresis. The desired SalI fragment ~2.8 kb.

B. Partial SalI Digestion of Plasmid pFJ124

The desired digestion was carried out in substantial accordance with the teaching of Example 6 except that plasmid pFJ124 and SalI restriction enzyme and reaction mix, rather than plasmid pLR1 and BamHI restriction enzyme and reaction mix, were used. The resultant DNZ precipitate was collected by centrifugation, rinsed in 70% ethanol, dried in vacuo, and then suspended in about 50 µl. of TE buffer.

C. Ligation

The ~2.8 kb SalI fragment of plasmid pIJ43 was ligated to the partial SalI digest of plasmid pFJ124 in substantial accordance with the teaching of Example 8C. The resultant DNA precipitate was collected by centrifugation, washed with 70% ethanol, collected again, and then suspended in 50 µl. of medium P for subsequent transformation.

Recombinant plasmids of two orientations result because the ~2.8 kb SalI fragment can be oriented in either direction. Plasmids pFJ148 and pFJ149 can be conventionally transformed into appropriate host cells and then identified by restriction enzyme and gel electrophoretic analysis.

EXAMPLE 30

Construction of *Streptomyces ambofaciens*/pFJ148 and *S. ambofaciens*/pFJ149

The desired constructions were made in substantial accordance with the teaching of Example 9 except that DNA from Example 29C, rather than DNA from Example 8C, was used. The desired transformants were selected for erythromycin resistance by overlaying the regenerating protoplasts with R2 medium top agar containing sufficient erythromycin to bring the plate concentration to 50 µg./ml. The resultant *Streptomyces ambofaciens*/pFJ148 and *S. ambofaciens*/pFJ149 erythromycin resistant colonies were isolated according to known procedures, cultured, tested for thiostrepton resistance, and then conventionally identified by restriction enzyme and gel electrophoretic analysis of the constitutive plasmids. The desired transformants were then conventionally cultured for subsequent production and isolation of plasmids pFJ148 and pFJ149. A restriction site map of each of plasmids pFJ148 and pFJ149 is presented in FIG. 16 of the accompanying drawings.

EXAMPLE 31

Construction of Plasmids pFJ150 and pFJ151

A. BamHI Digestion of Plasmids pBR322 and pFJ147

The desired digestions are each carried out in substantial accordance with the teaching of Example 2B except that BamHI restriction enzyme and reaction mix, rather than HindIII restriction enzyme and reaction mix, are used.

B. Ligation

The ligation of BamHI digested plasmid pBR322 and pFJ147 is carried out in substantial accordance with the teaching of Example 8C. The desired chimeric plasmid DNA is collected by centrifugation, washed with 70% ethanol, dried in vacuo, and then suspended in 50 µl. of TE buffer. Recombinant plasmids of two orientations result because the restricted plasmid pBR322 can be oriented in either direction. Plasmids pFJ150 and pFJ151 can be conventionally transformed into appropriate host cells and then identified by restriction enzyme and gel electrophoretic analysis.

EXAMPLE 32

Construction of *E. coli* K12 HB101/pFJ150 and *E. coli* K12 HB101/pFJ151

The desired constructions are made in substantial accordance with the teaching of Example 19 except that plasmids pFJ150 and pFJ151, rather than plasmids pEL121 and pEL122, are used. Surviving colonies are first selected, tested for the expected phenotype (Amp$^R$, Tet$^S$), and then conventionally identified as the desired *E. coli* K12 HB101/pFJ150 and *E. coli* K12 HB101/pFJ151 transformants by restriction enzyme and gel electrophoretic analysis of the constitutive plasmids. A restriction site map of each of plasmids pFJ150 and pFJ151 is presented in FIG. 16 of the accompanying drawings.

EXAMPLE 33

Construction of *Streptomyces ambofaciens*/pFJ150

The desired construction is made in substantial accordance with the teaching of Example 9 except that plasmid pFJ150 (isolated conventionally from *E. coli* K12 HB101/pFJ150 from Example 32), rather than DNA from Example 8C, is used.

EXAMPLE 34

Construction of *Streptomyces ambofaciens*/pFJ151

The desired construction is made in substantial accordance with the teaching of Example 9 except that plasmid pFJ151 (isolated conventionally from *E. coli* K12 HB101/pFJ151 from Example 32), rather than DNA from Example 8C, is used.

Representative plasmids and transformants constructed in accordance with the foregoing teaching include the following listed in Tables 1 and 2 below.

TABLE 1

Representative Plasmids

| Example No. | Plasmid Name | ~Size in kb | Construction |
|---|---|---|---|
| 35 | pFJ152 | 6.9 | BclI-BamHI deletion of pFJ145 |
| 36* | pFJ153 | 8.3 | Ligation of pBR322 BamHI fragment into BamHI digested pFJ124 |
| 37* | pFJ154** | 11.7 | Ligation of pBR322 BamHI fragment into BamHI (partial) digested pFJ144 |
| 38* | pFJ155** | 11.7 | Ligation of pBR325 BamHI fragment into BamHI (partial) digested pFJ145 |
| 39 | pFJ156 | 8.3 | Reverse orientation of pFJ153 |
| 40 | pFJ157 | 11.7 | Reverse orientation of pFJ154 |
| 41 | pFJ158 | 11.7 | Reverse orientation of pFJ155 |
| 42 | pFJ159 | 6.5 | Ligation of ~2.7 kb pIJ43 SalI-BglII fragment into SalI-BclI digested pFJ124 |
| 43* | pFJ160*** | 11.0 | Ligation of pBR322 BamHI fragment into BamHI (partial) digested pFJ159 |
| 44 | pFJ161 | 11.0 | Reverse orientation of pFJ160 |
| 45* | pFJ162*** | 11.3 | Ligation of pBR325 BamHI fragment into BamHI (partial) digested pFJ148 |
| 46 | pFJ163 | 11.3 | Reverse orientation of pFJ162 |
| 47* | pFJ177*** | 11.3 | Ligation of pBR322 BamHI fragment into BamHI (partial) digested pFJ149 |
| 48 | pFJ178 | 11.3 | Reverse orientation of pFJ177 |
| 49* | pFJ179 | 7.1 | Ligation of pBR322 BamHI fragment into ~2.8 kb BamHI fragment of pEL105 |

TABLE 1-continued

Representative Plasmids

| Example No. | Plasmid Name | ~Size in kb | Construction |
|---|---|---|---|
| 50 | pFJ180 | 7.1 | Reverse orientation of pFJ179 |
| 51 | pFJ191 | 3.5 | BclI-BamHI deletion of pFJ124 |

Figure 16:
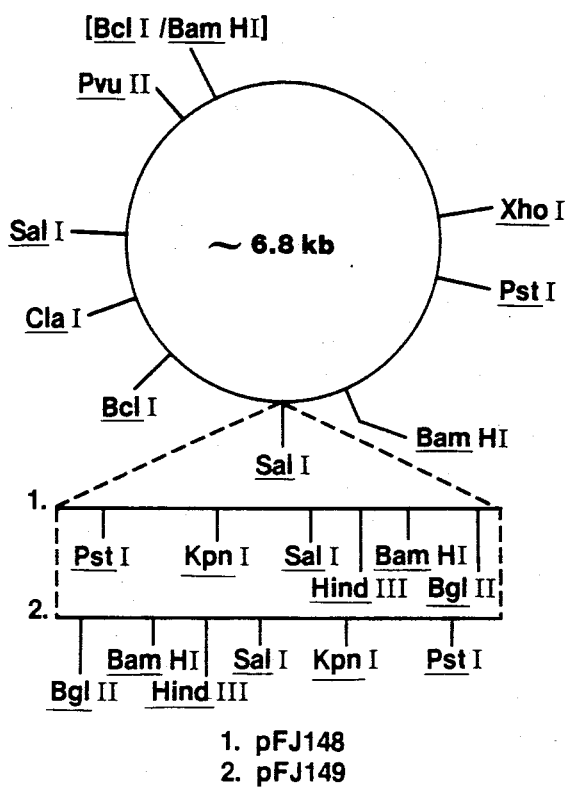
Figure 16:
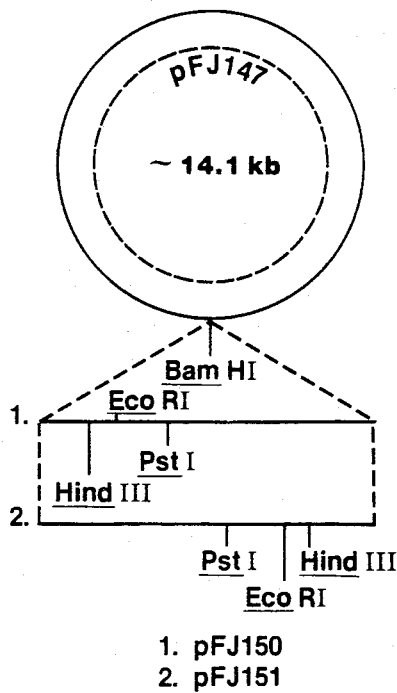

*The orientation of the pBR DNA is the same as that shown in FIG. 16 for pFJ150.
**The insertion at the BamHI site is such that the pBR DNA is between the neomycin resistance gene and the BclI site of the thiostrepton resistance gene.
***The insertion at the BamHI site is such that the pBR DNA is between the erythromycin resistance gene and the pFJ PstI site.

TABLE 2

Representative Transformants

1. Streptomyces R/R$^1$ wherein R is *ambofaciens, aureofaciens, griseofuscus, fradiae, lividans, granuloruber, tenebrarius* or *cinnamonensis* and wherein R$^1$ independently is a pFJ plasmid listed in Table 1.
2. E. coli R$^2$/R$^3$ wherein R$^2$ is K12 or K12 HB101 and wherein R$^3$ independently is plasmid pFJ153, pFJ154, pFJ155, pFJ156, pFJ157, pFJ158, pFJ160, pFJ161, pFJ162, pFJ163, pFJ177, pFJ178, pFJ179, or pFJ180.

I claim:

1. A recombinant DNA cloning vector comprising:
   (a) a functional origin of replication-containing restriction fragment of plasmid pEL103, and
   (b) one or more DNA segments that convey resistance to at least one antibiotic when transformed into a sensitive restrictionless host cell, said host cell being susceptible to transformation, cell division, and culture.
2. The cloning vector of claim 1 wherein the restriction fragment of pEL103 is the 2.8 kb BamHI restriction fragment.
3. The cloning vector of claim 1 wherein the restriction fragment of pEL103 is the 19.9 kb BamHI restriction fragment.
4. The cloning vector of claim 1, 2, or 3 wherein the one or more DNA segments that convey antibiotic resistance are selected from the group of segments that convey resistance to either or both of antibiotics thiostrepton and neomycin.
5. The cloning vector of claim 4 wherein one DNA segment conveys antibiotic resistance to thiostrepton.
6. The cloning vector of claim 4 wherein one DNA segment conveys antibiotic resistance to neomycin.
7. The cloning vector of claim 1, 2, or 3 wherein the one or more DNA segments that convey antibiotic resistance are selected from the group consisting of the 1.6 kb BamHI restriction fragment of plasmid pLR2 and the 3.4 kb BamHI restriction fragment of plasmid pLR1.
8. The cloning vector of claim 7 wherein one DNA segment is the 1.6 kb BamHI restriction fragment of plasmid pLR2.
9. The cloning vector of claim 7 wherein one DNA segment is the 3.4 kb BamHI restriction fragment of plasmid pLR1.
10. The recombinant DNA cloning vector of claim 1 selected from the group consisting of plasmids pEL107, pEL105, pEL109, pEL110, pEL113, pEL114, pEL115, pEL116, pEL108, pEL104, pEL111, pEL112, pEL117, pEL118, pEL119, and pEL120.
11. The cloning vector of claim 10 which is pEL107.
12. The cloning vector of claim 10 which is pEL105.
13. The cloning vector of claim 10 which is pEL109.
14. The cloning vector of claim 10 which is pEL110.
15. The cloning vector of claim 10 which is pEL113.
16. The cloning vector of claim 10 which is pEL114.
17. The cloning vector of claim 10 which is pEL115.
18. The cloning vector of claim 10 which is pEL116.
19. The cloning vector of claim 10 which is pEL108.
20. The cloning vector of claim 10 which is pEL104.
21. The cloning vector of claim 10 which is pEL111.
22. The cloning vector of claim 10 which is pEL112.
23. The cloning vector of claim 10 which is pEL117.
24. The cloning vector of claim 10 which is pEL118.
25. The cloning vector of claim 10 which is pEL119.
26. The cloning vector of claim 10 which is pEL120.
27. A functional origin of replication-containing restriction fragment of plasmid pEL103.
28. The 2.8 kb BamHI restriction fragment of plasmid pEL103.
29. A recombinant DNA cloning vector comprising:
   (a) a functional origin of replication-containing restriction fragment of plasmid pEL103,
   (b) one or more DNA segments that convey resistance to at least one antibiotic when transformed into a sensitive restrictionless host cell, said host cell being susceptible to transformation, cell division, and culture, and
   (c) a functional replicon-containing and antibiotic resistance-conferring restriction fragment of an *E. coli* plasmid.
30. The plasmid of claim 29 wherein the *E. Coli* plasmid is plasmid pBR322.
31. The plasmid of claim 30 which is plasmid pEL122.
32. A transformed restrictionless host cell comprising a recombinant DNA cloning vector of claim 1.
33. The transformed host cell of claim 32 which is selected from the group consisting of restrictionless cells of Streptomyces, Streptosporangium, Actinoplanes, Nocardia, Micromonospora, Bacillus, and Staphylococcus.
34. The transformed host cell of claim 33 which is a Streptomyces.
35. The transformed host cell of claim 33 which is a Streptosporangium.
36. The transformed host cell of claim 33 which is a Actinoplanes.
37. The transformed host cell of claim 33 which is a Nocardia.
38. The transformed host cell of claim 33 which is a Micromonospora.
39. The transformed host cell of claim 33 which is a Bacillus.
40. The transformed host cell of claim 33 which is a Staphylococcus.
41. The transformed host cell of claim 32 in which the recombinant DNA cloning vector is selected from the group consisting of plasmids pEL107, pEL105, pEL109, pEL110, pEL113, pEL114, pEL115, pEL116, pEL108, pEL104, pEL111, pEL112, pEL117, pEL118, pEL119, and pEL120.
42. The transformed host cell of claim 41 which is restrictionless Streptomyces.
43. The Streptomyces of claim 42 which is *Streptomyces fradiae*.
44. The Streptomyces of claim 42 which is *Streptomyces coelicolor*.
45. The transformed host cell of claim 42 which is *Streptomyces ambofaciens/pEL107*.

46. The transformed host cell of claim 42 which is *Streptomyces ambofaciens*/pEL105.

47. The transformed host cell of claim 42 which is *Streptomyces ambofaciens*/pEL109.

48. The transformed host cell of claim 42 which is *Streptomyces ambofaciens*/pEL110.

49. The tranformed host cell of claim 42 which is *Streptomyces ambofaciens*/pEL113.

50. The transformed host cell of claim 42 which is *Streptomyces ambofaciens*/pEL114.

51. The transformed host cell of claim 42 which is *Streptomyces ambofaciens*/pEL115.

52. The transformed host cell of claim 42 which is *Streptomyces ambofaciens*/pEL116.

53. The transformed host cell of claim 42 which is *Streptomyces ambofaciens*/pEL108.

54. The transformed host cell of claim 42 which is *Streptomyces ambofaciens*/pEL104.

55. The transformed host cell of claim 42 which is *Streptomyces ambofaciens*/pEL111.

56. The transformed host cell of claim 42 which is *Streptomyces ambofaciens*/pEL112.

57. The transformed host cell of claim 42 which is *Streptomyces ambofaciens*/pEL117.

58. The transformed host cell of claim 42 which is *Streptomyces ambofaciens*/pEL118.

59. The transformed host cell of claim 42 which is *Streptomyces ambofaciens*/pEL119.

60. The transformed host cell of claim 42 which is *Streptomyces ambofaciens*/pEL120.

61. A transformed restrictionless host cell comprising a recombinant DNA cloning vector of claim 29.

62. The transformed host cell of claim 61 wherein the replicon-containing and resistance-conferring restriction fragment in the vector is a restriction fragment of plasmid pBR322.

63. The transformed host cell of claim 61 which is *Streptomyces ambofaciens*/pEL121.

64. The transformed host cell of claim 61 which is restrictionless Streptomyces.

65. The transformed host cell of claim 61 which is *E. coli*.

66. The transformed host cell of claim 61 which is *E. coli* K12 HB101/pEL121.

67. The transformed host cell of claim 61 which is *E. coli* K12 HB101/pEL122.

68. The recombinant DNA cloning vector of claim 1 wherein one DNA segment conveys resistance to antibiotic erythromycin.

69. The recombinant DNA cloning vector of claim 68 in which the DNA segment is a restriction fragment of plasmid pIJ43.

70. The recombinant DNA cloning vector of claim 1 which is selected from the group consisting of plasmid pFJ124, pFJ144, pFJ145, pFJ146, pFJ147, pFJ148, pFJ149, pFJ152 and pFJ159.

71. The recombinant DNA cloning vector of claim 70 which is plasmid pFJ124.

72. The recombinant DNA cloning vector of claim 70 which is plasmid pFJ144.

73. The recombinant DNA cloning vector of claim 70 which is plasmid pFJ146.

74. The recombinant DNA cloning vector of claim 70 which is plasmid pFJ147.

75. The recombinant DNA cloning vector of claim 70 which is plasmid pFJ148.

76. The recombinant DNA cloning vector of claim 29 wherein a DNA segment conveys resistance to antibiotic erythromycin.

77. The recombinant DNA cloning vector of claim 76 in which the DNA segment is a restriction fragment of plasmid pIJ43.

78. The recombinant DNA cloning vector of claim 29 which is selected from the group consisting of plasmid pFJ150, pFJ151, pFJ153, pFJ155, pFJ156, pFJ157, pFJ158, pFJ160, pFJ161, pFJ162, pFJ163, pFJ177, pFJ178, pFJ179 and pFJ180.

79. The recombinant DNA cloning vector of claim 78 which is plasmid pFJ150.

80. The recombinant DNA cloning vector of claim 78 which is plasmid pFJ153.

81. The recombinant DNA cloning vector of claim 78 which is plasmid pFJ155.

82. The recombinant DNA cloning vector of claim 78 which is plasmid pFJ160.

83. The recombinant DNA cloning vector of claim 78 which is plasmid pFJ179.

84. A transformed restrictionless host cell comprising a recombinant DNA cloning vector of claim 70.

85. The transformed host cell of claim 84 which is Streptomyces.

86. The transformed host cell of claim 84 which is *Streptomyces ambofaciens*/pFJ124.

87. The transformed host cell of claim 84 which is *Streptomyces ambofaciens*/pFJ144.

88. The transformed host cell of claim 84 which is *Streptomyces ambofaciens*/pFJ146.

89. The transformed host cell of claim 84 which is *Streptomyces ambofaciens*/pFJ147.

90. The transformed host cell of claim 84 which is *Streptomyces ambofaciens*/pFJ148.

91. A transformed restrictionless host cell comprising a recombinant DNA cloning vector of claim 78.

92. The transformed host cell of claim 91 which is *E. coli* K12 HB101/pFJ150.

93. The transformed host cell of claim 91 which is *E. coli* K12 HB101/pFJ153.

94. The transformed host cell of claim 91 which is *E. coli* K12 HB101/pFJ155.

95. The transformed host cell of claim 91 which is *E. coli* K12 HB101/pFJ160.

96. The transformed host cell of claim 91 which is *E. coli* K12 HB101/pFJ179.

97. A transformed restrictionless host cell which is Streptomyces R/R$^1$ wherein R is *ambofaciens, griseofuscus, lividans, fradiae, aureofaciens, tenebrarius* or *cinnamonensis* and wherein R$^1$ independently is a recombinant DNA cloning vector of claim 70.

* * * * *